United States Patent
Hermann et al.

(10) Patent No.: US 12,357,418 B2
(45) Date of Patent: Jul. 15, 2025

(54) SURGICAL IMPLANT FOR MARKING SOFT TISSUE

(71) Applicant: HOLOGIC, INC., Marlborough, MA (US)

(72) Inventors: George D. Hermann, Los Altos Hills, CA (US); David B. Willis, Mountain View, CA (US); Michael J. Drews, Palo Alto, CA (US); Gail S. Lebovic, Frisco, TX (US); James B. Stubbs, Palo Alto, CA (US)

(73) Assignee: HOLOGIC, INC., Marlborough, MA (US)

( * ) Notice: Subject to any disclaimer, the term of this patent is extended or adjusted under 35 U.S.C. 154(b) by 0 days.

(21) Appl. No.: 18/593,019

(22) Filed: Mar. 1, 2024

(65) Prior Publication Data
US 2024/0277445 A1    Aug. 22, 2024

Related U.S. Application Data

(63) Continuation of application No. 17/953,996, filed on Sep. 27, 2022, now Pat. No. 11,944,509, which is a
(Continued)

(51) Int. Cl.
*A61B 5/00*        (2006.01)
*A61B 90/00*       (2016.01)
(Continued)

(52) U.S. Cl.
CPC ............ *A61B 90/39* (2016.02); *A61N 5/1015* (2013.01); *A61B 2017/00004* (2013.01);
(Continued)

(58) Field of Classification Search
CPC ............ A61B 90/39; A61B 2090/3908; A61B 2090/3925; A61B 2090/3954; A61B 2090/3966
See application file for complete search history.

(56) References Cited

U.S. PATENT DOCUMENTS 3,157,524 A   11/1964 Artandi
3,520,402 A    7/1970 Nichols
(Continued)

FOREIGN PATENT DOCUMENTS

EP      1997457       12/2008
JP      2008515592     5/2008
(Continued)

OTHER PUBLICATIONS

Appeal Brief (replacement) filed on Feb. 1, 2016, for U.S. Appl. No. 13/456,435, by Hermann et al., 14 pages.
(Continued)

*Primary Examiner* — Joel F Brutus
(74) *Attorney, Agent, or Firm* — Jones Robb, PLLC

(57) ABSTRACT

An implantable tissue marker device is provided to be placed in a soft tissue site through a surgical incision. The device can include a bioabsorbable body in the form of a spiral and defining a spheroid shape for the device, the spiral having a longitudinal axis, and turns of the spiral being spaced apart from each other in a direction along the longitudinal axis. A plurality of markers can be disposed on the body, the markers being visualizable by a radiographic imaging device. The turns of the spiral are sufficiently spaced apart to form gaps that allow soft tissue to infiltrate between the turns and to allow flexibility in the device along the longitudinal axis in the manner of a spring.

21 Claims, 29 Drawing Sheets

Related U.S. Application Data continuation of application No. 16/661,663, filed on Oct. 23, 2019, now Pat. No. 11,529,211, which is a continuation of application No. 15/920,126, filed on Mar. 13, 2018, now Pat. No. 10,500,014, which is a continuation of application No. 13/456,435, filed on Apr. 26, 2012, now abandoned.

(51) Int. Cl.
*A61N 5/10* (2006.01)
*A61B 17/00* (2006.01)
*A61F 2/12* (2006.01)
*G01R 33/58* (2006.01)

(52) U.S. Cl.
CPC ............... *A61B 2090/3908* (2016.02); *A61B 2090/3925* (2016.02); *A61B 2090/3954* (2016.02); *A61B 2090/3966* (2016.02); *A61F 2/12* (2013.01); *A61F 2240/005* (2013.01); *A61N 5/10* (2013.01); *F04C 2270/041* (2013.01); *G01R 33/58* (2013.01)

(56) References Cited

U.S. PATENT DOCUMENTS

| | | |
|---|---|---|
| 4,298,998 A | 11/1981 | Naficy |
| 4,832,686 A | 5/1989 | Anderson |
| 4,957,479 A | 9/1990 | Roemer |
| 5,019,087 A | 5/1991 | Nichols |
| 5,429,582 A | 7/1995 | Williams |
| 5,480,432 A | 1/1996 | Suding et al. |
| 5,501,706 A | 3/1996 | Arenberg |
| 5,545,229 A | 8/1996 | Parsons et al. |
| 5,607,477 A | 3/1997 | Schindler et al. |
| 5,626,611 A | 5/1997 | Liu et al. |
| 5,676,146 A | 10/1997 | Scarborough |
| 5,716,404 A | 2/1998 | Vacanti et al. |
| 5,853,366 A | 12/1998 | Dowlatshahi |
| 5,873,865 A | 2/1999 | Horzewski et al. |
| 6,030,333 A | 2/2000 | Sioshansi et al. |
| 6,071,301 A | 6/2000 | Cragg et al. |
| 6,080,099 A | 6/2000 | Slater et al. |
| 6,159,165 A | 12/2000 | Ferrera et al. |
| 6,161,034 A | 12/2000 | Burbank et al. |
| 6,174,330 B1 | 1/2001 | Stinson |
| 6,203,570 B1 | 3/2001 | Baeke |
| 6,214,045 B1 | 4/2001 | Corbitt, Jr. et al. |
| 6,228,055 B1 | 5/2001 | Foerster et al. |
| 6,234,177 B1 | 5/2001 | Barsch |
| 6,245,103 B1 | 6/2001 | Stinson |
| 6,270,464 B1 | 8/2001 | Fulton, III et al. |
| 6,340,367 B1 | 1/2002 | Stinson et al. |
| 6,356,782 B1 | 3/2002 | Sirimanne et al. |
| 6,363,940 B1 | 4/2002 | Krag |
| 6,371,904 B1 | 4/2002 | Sirimanne et al. |
| 6,477,423 B1 | 11/2002 | Jenkins |
| 6,575,991 B1 | 6/2003 | Chesbrough et al. |
| 6,579,310 B1 | 6/2003 | Cox et al. |
| 6,626,939 B1 | 9/2003 | Burnside et al. |
| 6,638,308 B2 | 10/2003 | Corbitt, Jr. et al. |
| 6,699,205 B2 | 3/2004 | Fulton et al. |
| 6,725,083 B1 | 4/2004 | Burbank et al. |
| 6,730,042 B2 | 5/2004 | Fulton et al. |
| 6,746,458 B1 | 6/2004 | Cloud |
| 6,766,186 B1 | 7/2004 | Hoyns et al. |
| 6,881,226 B2 | 4/2005 | Corbitt, Jr. et al. |
| 6,893,462 B2 | 5/2005 | Buskirk et al. |
| 6,993,375 B2 | 1/2006 | Burbank et al. |
| 7,047,063 B2 | 5/2006 | Burbank et al. |
| 7,229,417 B2 | 6/2007 | Foerster et al. |
| 7,424,320 B2 | 9/2008 | Chesbrough et al. |
| 7,547,274 B2 | 6/2009 | Rapach et al. |
| 7,572,287 B2 | 8/2009 | Stinson |
| 7,637,948 B2 | 12/2009 | Corbitt, Jr. |
| 7,670,350 B2 | 3/2010 | Selis |
| 7,837,612 B2 | 11/2010 | Gill et al. |
| 7,871,438 B2 | 1/2011 | Corbitt, Jr. |
| 7,875,059 B2 | 1/2011 | Patterson et al. |
| 7,972,261 B2 | 7/2011 | Lamoureux et al. |
| 7,972,619 B2 | 7/2011 | Fisher |
| 8,052,658 B2 | 11/2011 | Field |
| 8,060,183 B2 | 11/2011 | Leopold et al. |
| 8,114,006 B2 | 2/2012 | Cox et al. |
| 8,157,862 B2 | 4/2012 | Corbitt, Jr. |
| 8,320,993 B2 | 11/2012 | Sirimanne et al. |
| 8,486,028 B2 | 7/2013 | Field |
| 8,600,481 B2 | 12/2013 | Sirimanne et al. |
| 8,680,498 B2 | 3/2014 | Corbitt et al. |
| 9,014,787 B2 | 4/2015 | Stubbs et al. |
| 9,199,092 B2 | 12/2015 | Stubbs et al. |
| 9,615,915 B2 | 4/2017 | Lebovic et al. |
| 9,980,809 B2 | 5/2018 | Lebovic et al. |
| 10,500,014 B2 | 12/2019 | Hermann et al. |
| 11,337,772 B2 | 5/2022 | Stubbs |
| 11,752,361 B2 | 9/2023 | Stubbs et al. |
| 11,944,509 B2 | 4/2024 | Hermann et al. |
| 2001/0034528 A1 | 10/2001 | Foerster et al. |
| 2001/0041936 A1 | 11/2001 | Corbitt, Jr. et al. |
| 2001/0047164 A1 | 11/2001 | Teague et al. |
| 2002/0035324 A1 | 3/2002 | Sirimanne et al. |
| 2002/0072806 A1 | 6/2002 | Buskirk et al. |
| 2003/0083732 A1 | 5/2003 | Stinson |
| 2003/0195561 A1 | 10/2003 | Carley et al. |
| 2004/0109823 A1 | 6/2004 | Kaplan |
| 2004/0249457 A1 | 12/2004 | Smith et al. |
| 2005/0049489 A1 | 3/2005 | Foerster et al. |
| 2005/0074405 A1 | 4/2005 | Williams |
| 2005/0080338 A1 | 4/2005 | Sirimanne et al. |
| 2005/0080339 A1 | 4/2005 | Sirimanne et al. |
| 2005/0101860 A1 | 5/2005 | Patrick et al. |
| 2005/0113686 A1 | 5/2005 | Peckham |
| 2005/0143770 A1 | 6/2005 | Carter et al. |
| 2005/0165480 A1 | 7/2005 | Jordan et al. |
| 2005/0234336 A1 | 10/2005 | Beckman et al. |
| 2006/0025795 A1 | 2/2006 | Chesbrough et al. |
| 2006/0058570 A1 | 3/2006 | Rapach et al. |
| 2006/0116713 A1 | 6/2006 | Sepetka et al. |
| 2006/0173296 A1 | 8/2006 | Miller et al. |
| 2007/0021642 A1 | 1/2007 | Lamoureux et al. |
| 2007/0038014 A1 | 2/2007 | Cox et al. |
| 2007/0038017 A1 | 2/2007 | Chu |
| 2007/0104695 A1 | 5/2007 | Quijano et al. |
| 2007/0141111 A1* | 6/2007 | Suokas ............... A61L 27/44 424/426 |
| 2007/0167665 A1 | 7/2007 | Hermann et al. |
| 2007/0167668 A1 | 7/2007 | White et al. |
| 2007/0198021 A1 | 8/2007 | Wales |
| 2007/0219446 A1 | 9/2007 | Beyhan |
| 2008/0015472 A1 | 1/2008 | Ressemann et al. |
| 2008/0045773 A1 | 2/2008 | Popowski et al. |
| 2008/0082113 A1 | 4/2008 | Bishop et al. |
| 2008/0097199 A1 | 4/2008 | Mullen |
| 2008/0228164 A1 | 9/2008 | Nicoson et al. |
| 2008/0243226 A1 | 10/2008 | Fernandez et al. |
| 2008/0281388 A1 | 11/2008 | Corbitt et al. |
| 2009/0024225 A1 | 1/2009 | Stubbs |
| 2009/0030298 A1 | 1/2009 | Matthews et al. |
| 2009/0143747 A1 | 6/2009 | Dias et al. |
| 2009/0149833 A1 | 6/2009 | Cima et al. |
| 2009/0319046 A1 | 12/2009 | Krespi et al. |
| 2009/0326577 A1 | 12/2009 | Johnson et al. |
| 2010/0010341 A1 | 1/2010 | Talpade et al. |
| 2010/0030072 A1 | 2/2010 | Casanova et al. |
| 2010/0042104 A1 | 2/2010 | Kota et al. |
| 2010/0222802 A1 | 9/2010 | Gillespie, Jr. et al. |
| 2011/0004094 A1 | 1/2011 | Stubbs et al. |
| 2011/0028831 A1 | 2/2011 | Kent |
| 2011/0130655 A1 | 6/2011 | Nielson et al. |
| 2011/0313288 A1* | 12/2011 | Chi Sing ............ A61B 8/0825 600/437 |
| 2012/0059285 A1 | 3/2012 | Soltani et al. |
| 2012/0116215 A1 | 5/2012 | Jones et al. |
| 2012/0123535 A1 | 5/2012 | Alejandro |

(56) References Cited

U.S. PATENT DOCUMENTS

| | | |
|---|---|---|
| 2012/0130489 A1 | 5/2012 | Chernomorsky et al. |
| 2013/0032962 A1 | 2/2013 | Liu et al. |
| 2013/0289389 A1 | 10/2013 | Hermann et al. |
| 2013/0289390 A1 | 10/2013 | Hermann et al. |
| 2013/0317275 A1 | 11/2013 | Stubbs |
| 2014/0100656 A1 | 4/2014 | Namnoum et al. |
| 2014/0200396 A1 | 7/2014 | Lashinski et al. |
| 2014/0275984 A1 | 9/2014 | Hermann et al. |
| 2015/0112194 A1 | 4/2015 | Stubbs |
| 2015/0112434 A1 | 4/2015 | Felix et al. |
| 2015/0250582 A1 | 9/2015 | Cgeenhalgh et al. |
| 2015/0313708 A1 | 11/2015 | Mayo Martin |
| 2016/0022416 A1 | 1/2016 | Felix et al. |
| 2016/0082286 A1 | 3/2016 | Stubbs et al. |
| 2016/0242899 A1 | 8/2016 | Lee et al. |
| 2017/0181842 A1 | 6/2017 | Lebovic et al. |
| 2017/0181843 A1 | 6/2017 | Lebovic et al. |
| 2017/0181844 A1 | 6/2017 | Lebovic et al. |
| 2017/0181845 A1 | 6/2017 | Lebovic et al. |
| 2018/0036096 A1 | 2/2018 | Stubbs |
| 2018/0092703 A1 | 4/2018 | Rodriguez-Navarro et al. |
| 2018/0200020 A1 | 7/2018 | Hermann et al. |
| 2019/0336274 A1 | 11/2019 | Lebovic et al. |
| 2019/0358468 A1 | 11/2019 | Stubbs et al. |
| 2020/0113647 A1 | 4/2020 | Hermann et al. |
| 2023/0093141 A1 | 3/2023 | Hermann et al. |
| 2023/0157810 A1 | 5/2023 | Lebovic et al. |

FOREIGN PATENT DOCUMENTS

| | | |
|---|---|---|
| JP | 2008143896 | 6/2008 |
| JP | 2008538303 | 10/2008 |
| JP | 2009500089 | 1/2009 |
| JP | 2012528687 | 11/2012 |
| WO | 3030534 | 6/2000 |
| WO | 9818408 | 6/2000 |
| WO | 2006044132 | 4/2006 |
| WO | 2006110733 | 10/2006 |
| WO | 2007000756 | 1/2007 |
| WO | 2007006303 | 1/2007 |
| WO | 2010141422 | 12/2010 |
| WO | 2012122215 | 9/2012 |
| WO | 2013009282 | 1/2013 |
| WO | 2013163381 | 10/2013 |
| WO | 2016014990 | 1/2016 |

OTHER PUBLICATIONS

Corrected Notice of Allowability mailed on Apr. 4, 2018, for U.S. Appl. No. 15/456,078, filed Mar. 10, 2017, 4 pages.
Corrected Notice of Allowability mailed on May 2, 2018, for U.S. Appl. No. 15/456,078, filed Mar. 10, 2017, 4 pages.
Examiners Answer to Appeal Brief mailed on Sep. 14, 2016, for U.S. Appl. No. 13/456,435 by Hermann et al., 23 pages.
Extended European Search Report mailed on Nov. 30, 2015, for EP Application No. 13782314.2 filed on Apr. 25, 2013, 7 pages.
Extended European Search Report mailed on Jan. 23, 2015, for EP Application No. 10783902.9, filed on Jun. 1, 2010, 5 pages.
Extended European Search Report mailed on Dec. 22, 2017, for EP Application No. 15825567.9, filed on Jul. 24, 2015, 8 pages.
Final Office Action mailed on Jan. 22, 2015, for U.S. Appl. No. 13/456,435, filed Apr. 26, 2012, 22 pages.
Office Action mailed on Nov. 6, 2013, for U.S. Appl. No. 13/656,068, filed Oct. 19, 2012, 14 pages.
Final Office Action mailed on Dec. 17, 2014, for U.S. Appl. No. 13/656,068, filed Oct. 19, 2012, 16 pages.
Final Office Action mailed on Mar. 21, 2016, for U.S. Appl. No. 13/802,041, filed Mar. 13, 2013, 9 pages.
Final Office Action mailed on Aug. 22, 2013, for U.S. Appl. No. 12/790,314, filed May 28, 2010, 24 pages.
Final Office Action mailed on Jun. 27, 2014, for U.S. Appl. No. 12/173,881, filed Jul. 16, 2008, 18 pages.
Final Office Action mailed on Oct. 11, 2016, for U.S. Appl. No. 14/808,852, filed Jul. 24, 2015, 13 pages.
Final Office Action mailed on May 10, 2017, for U.S. Appl. No. 13/656,068, filed Oct. 19, 2012, 18 pages.
Final Office Action mailed on Oct. 6, 2017, for U.S. Appl. No. 15/455,977, filed Mar. 10, 2017, 14 pages.
Final Office Action mailed on Oct. 16, 2017, 2017, for U.S. Appl. No. 15/455,994, filed Mar. 10, 2017, 11 pages.
Final Office Action mailed on Oct. 20, 2017, for U.S. Appl. No. 14/954,589, filed Nov. 30, 2015, 33 pages.
Final Office Action mailed on Nov. 14, 2017, for U.S. Appl. No. 15/456,030, filed Mar. 10, 2017, 14 pages.
Final Office Action mailed on Nov. 17, 2017, for U.S. Appl. No. 15/466,619, filed Mar. 22, 2017, 16 pages.
Final Office Action mailed on Dec. 20, 2017, for U.S. Appl. No. 13/656,068, filed Oct. 19, 2012, 16 pages.
Hudson Tech Files. (2015). "Thermoset vs Thermoplastic: Heat Affects Polymers," RL Hudson & Company, located at ittp://www.dhudson.com/thermoplastic-vs-hermoset.html#sthash.ORtnThLj.W32KgPSn.dpbs, 1 total page.
International Search Report mailed on Mar. 10, 2014 for PCT Patent Application No. PCT/US13/64168 filed on Oct. 9, 2013, 4 pages.
International Search Report mailed on Jul. 9, 2013, for PCT Application No. PCT/US2013/38145, Apr. 25, 2013, 2 pages.
International Search Report mailed on Jul. 28, 2010, for PCT Application No. PCT/US2010/036828, filed on Jun. 1, 2010, 2 pages.
International Search Report mailed on Oct. 28, 2015, for PCT Application No. PCT/US2015/042082, filed on Jul. 24, 2015, 2 pages.
Lakeshore Biomaterials, "General Mechanical Properties Chart". Feb. 19, 2009, 1 page.
Middleton, J., "Tailoring of Poly(lactide-co-glycolide) to Control Properties", Lakeshore Biomaterials, 2007, 67 pages.
Medical Device Daily, (Sep. 30, 2005) The Medical Technology Newspaper 9(188):pp. 1 and 9 (2 pages).
Non-Final Office Action mailed Apr. 25, 2014, for U.S. Appl. No. 13/456,435, filed Apr. 26, 2012, 17 pages.
Non-Final Office Action mailed Aug. 27, 2015, for U.S. Appl. No. 13/802,041, filed Mar. 13, 2013, 9 pages.
Non-Final Office Action mailed on Mar. 22, 2013, for U.S. Appl. No. 13/656,068, filed Oct. 19, 2012, 17 pages.
Non-Final Office Action mailed on Apr. 3, 2014, for U.S. Appl. No. 13/656,068, filed Oct. 19, 2012, 12 pages.
Non-Final Office Action mailed on Dec. 1, 2015, for U.S. Appl. No. 13/656,068, filed Oct. 19, 2012, 23 pages.
Non-Final Office Action mailed on Jan. 3, 2013, for U.S. Appl. No. 12/790,314, filed May 28, 2010, 11 pages.
Non-Final Office Action mailed on Oct. 10, 2014, for U.S. Appl. No. 12/790,314, filed May 28, 2010, 7 pages.
Non-Final Office Action mailed on May 8, 2015, for U.S. Appl. No. 14/581,146, filed on Dec. 23, 2014, 10 pages.
Non-Final Office Action mailed on Aug. 16, 2011, for U.S. Appl. No. 12/173,881, filed Jul. 16, 2008, 12 pages.
Non-Final Office Action mailed on Sep. 23, 2016, for U.S. Appl. No. 14/581,807, filed Dec. 23, 2014, 16 pages.
Non-Final Office Action mailed on Mar. 25, 2016, for U.S. Appl. No. 14/808,852, filed Jul. 24, 2015, 11 pages.
Non-Final Office Action mailed on Jun. 29, 2016, for U.S. Appl. No. 14/808,852, filed Jul. 24, 2015 14 pages.
Non-Final Office Action mailed on Jan. 5, 2017, for U.S. Appl. No. 14/954,589, filed Nov. 30, 2015, 12 pages.
Non-Final Office Action mailed on May 5, 2017, for U.S. Appl. No. 15/455,994, filed Mar. 10, 2017, 11 pages.
Non-Final Office Action mailed on May 5, 2017, for U.S. Appl. No. 15/456,030, filed Mar. 10, 2017, 12 pages.
Non-Final Office Action mailed on Apr. 21, 2017, for U.S. Appl. No. 15/456,078, filed Mar. 10, 2017, 10 pages.
Non-Final Office Action mailed on May 24, 2017, for U.S. Appl. No. 15/455,977, filed Mar. 10, 2017, 13 pages.
Non-Final Office Action mailed on Aug. 31, 2017, for U.S. Appl. No. 15/456,078, filed Mar. 10, 2017, 8 pages.

(56) References Cited

OTHER PUBLICATIONS

Notice of Allowance mailed on Sep. 25, 2015, for U.S. Appl. No. 14/581,146, filed Dec. 23, 2014, 9 pages.
Notice of Allowance mailed on Mar. 17, 2015, for U.S. Appl. No. 12/790,314, filed May 28, 2010, 8 pages.
Notice of Allowance mailed on Feb. 1, 2017, for U.S. Appl. No. 14/808,852, filed on Jul. 24, 2015, 7 pages.
Notice of Allowance mailed on Oct. 25, 2017, for U.S. Appl. No. 15/456,078, filed Mar. 10, 2017, 5 pages.
Notice of Allowance mailed on Feb. 28, 2018 for U.S. Appl. No. 15/456,078, filed Mar. 10, 2017, 2 pages.
Author unknown, "Purasorb® Technology", Purac Biomaterials, 2009, 1 page.
Reply Brief filed on Nov. 14, 2016, for U.S. Appl. No. 13/456,435, by Hermann et al., 5 pages.
Supplemental Notice of Allowability mailed on Mar. 10, 2017, for U.S. Appl. No. 14/808,852, filed Jul. 24, 2015, 2 pages.
Written Opinion of the International Searching Authority mailed on Jul. 9, 2013, for PCT Application No. PCT/US2013/38145, Apr. 25, 2013, 6 pages.
Written Opinion mailed on Mar. 10, 2014 for PCT Patent Application No. PCT/US13/64168, filed on Oct. 9, 2013, 6 pages.
Written Opinion of the International Searching Authority mailed on Jul. 28, 2010, for PCT Application No. PCT/US2010/036828, filed on Jun. 1, 2010, 6 pages.
Written Opinion of the International Searching Authority mailed on Oct. 28, 2015, for PCT Application No. PCT/US2015/042082, filed on Jully 24, 2015, 4 pages.
Final Office Action mailed on Dec. 27, 2018, for U.S. Appl. No. 15/920,126, filed on Mar. 13, 2018, 18 pages.
Non-Final Office Action mailed on Aug. 1, 2018, for U.S. Appl. No. 14/954,589, filed Nov. 30, 2015, 16 pages.
Non-Final Office Action mailed on Oct. 23, 2018, for U.S. Appl. No. 13/656,068, filed pn Oct. 19, 2012, 22 pages.
Non-Final Office Action mailed on May 3, 2018, for U.S. Appl. No. 15/920,126, filed on Mar. 13, 2018, 15 pages.
Final Office Action dated Nov. 10, 2020 in U.S. Appl. No. 15/982,903.
Office Action dated May 4, 2021 in U.S. Appl. No. 15/982,903.
Final Office Action dated Aug. 26, 2021 in U.S. Appl. No. 15/982,903.
Office Action dated Mar. 9, 2021 in U.S. Appl. No. 16/262,401.
Office Action dated Jun. 25, 2021 in U.S. Appl. No. 16/262,401.
Final Office Action dated Aug. 30, 2021 in U.S. Appl. No. 16/262,401.
Office Action dated Dec. 6, 2021 in U.S. Appl. No. 16/518,139.
Office Action dated Dec. 13, 2021 in U.S. Appl. No. 16/262,401.
Office Action dated Mar. 25, 2021 in U.S. Appl. No. 16/262,401.
Notice of Allowance dated Jan. 26, 2022 in U.S. Appl. No. 15/982,903.
Office Action dated Mar. 3, 2022 in U.S. Appl. No. 16/661,663.
Final Office Action dated Jun. 14, 2022 in U.S. Appl. No. 16/518,139.
Bouman, Reconstruction of the breast after subcutaneous mastectomy. Possibilities and problems, 1974, Achivum Chirurgicum Neerlandicum, 26, 4:343-352 (Year: 1974).
Notice of Allowance dated Jun. 27, 2022 in U.S. Appl. No. 16/661,663, 7 pages.
Extended European Search Report dated Jul. 22, 2022 for EP 22173509.5, 8 pages.
Notice of Allowance dated Aug. 31, 2022 in U.S. Appl. No. 16/518,139, 8 pages.
Office Action dated Oct. 20, 2022 from U.S. Appl. No. 16/262,401, 13 pages.
Application and Drawings filed Nov. 21, 2022 from U.S. Appl. No. 18/057,459.
Final Office Action dated Jan. 24, 2023 in U.S. Appl. No. 16/262,401.
Notice of Allowance dated Apr. 4, 2023 in U.S. Appl. No. 16/262,401.
Office Action dated Apr. 11, 2023 from U.S. Appl. No. 17/953,996, 14 pp.
Final Office Action dated Jul. 13, 2023 from U.S. Appl. No. 17/953,996, 12 pp.
Advisory Action dated Oct. 13, 2023 from U.S. Appl. No. 17/953,996, 3 pp.
Notice of Allowance dated Nov. 29, 2023 from U.S. Appl. No. 17/953,996.
Office Action dated Oct. 1, 2024 in U.S. Appl. No. 18/057,459, 12 pp.

\* cited by examiner

SURGICAL IMPLANT FOR MARKING SOFT TISSUE

CROSS-REFERENCE TO RELATED APPLICATIONS

This application is a continuation of U.S. patent application Ser. No. 17/953,996, filed on Sep. 27, 2022, which application is a continuation of U.S. patent application Ser. No. 16/661,663, filed on Oct. 23, 2019, now U.S. Pat. No. 11,529,211, which application is a continuation of U.S. patent application Ser. No. 15/920,126, filed on Mar. 13, 2018, now U.S. Pat. No. 10,500,014, which application is a continuation of U.S. patent application Ser. No. 13/456,435, filed on Apr. 26, 2012, now abandoned, the entire contents each of which are incorporated by reference herein.

This application incorporates by reference United States patent publication no. 2009-0024225-A1, entitled "Implant for Targeting Therapeutic Procedure," filed on Jul. 16, 2008, which application is incorporated herein by reference in its entirety.

This application incorporates by reference United States patent publication no. 2011-0004094 A1, entitled "Bioabsorbable Target for Diagnostic or Therapeutic Procedure," filed on May 28, 2010, which application is incorporated herein by reference in its entirety.

BACKGROUND

Two trends have become significant in driving the delivery of medical treatments: First, treatments, be they drugs, energy or surgery, are moving towards local and more precise (i.e., focused) delivery, and second, treatments are being tailored and optimized for each patient based on their specific anatomy, physiology and disease features. These directions both are designed to minimize the likelihood of adverse effects from the therapies as well as provide a more patient-specific treatment, which may improve disease-free survival rates and/or improve/decrease local recurrence of disease.

Many of these trends have been adopted in the surgical environment where large, open surgical procedures have been and continue to be replaced by laparoscopic techniques and other minimally invasive procedures. Drug therapies are moving toward more localized delivery as well, such as treatments that are placed directly at or near the treatment site (e.g., drug eluting stents and GLIADEL wafers for brain tumors). Until recently, the desire to do the same in radiation therapy has been hampered by inadequate technology for focused delivery. However, significant progress in the delivery of radiation to a more localized region of treatment (i.e., localized radiation delivery) has become popularized in the field of brachytherapy, a subspecialty of radiation oncology, most notably used in the treatment of prostate, breast, and gynecologic cancer patients. As an example, in breast brachytherapy, the radiation source is temporarily inserted into one or more catheters that are temporarily placed and held within the breast at the site where the tumor has been removed. The prescribed dose of radiation is calculated and customized for each patient, and is delivered directly to the area at highest risk of local recurrence. This system allows for more accurately directed treatment, which is effectively delivered from the "inside out." This approach has gained popularity because it offers a number of benefits to patients undergoing treatment for breast cancer including delivery of the equivalent dose of radiation in a shorter timeframe (normally 5-7 days vs. daily for up to 6 weeks) and delivery to a smaller volume of the breast tissue (i.e., accelerated and smaller volume treatments). Thus, by delivering a customized and focused amount of radiation, the therapeutic advantage is maintained while the potential damage to surrounding normal tissues is minimized.

Although brachytherapy is gaining acceptance throughout the world, external beam radiation therapy (EBRT) remains the most common method of delivery for radiation therapy. EBRT is used in the treatment of many different types of cancers, and can be delivered before, during and/or after surgery. In addition, chemotherapy is often utilized in conjunction with radiation therapy. EBRT is delivered to cancer patients as either the first line of therapy (for non-resected cancers) or as a means of maximizing local control of the cancer following surgical removal of the tumor. The radiation is meant to help "sterilize" the area of tumor resection in an effort to decrease the potential for recurrent disease.

In EBRT, one or more beams of high energy x-rays are aimed at the part of the body needing treatment with radiation. A linear accelerator (often called a linac) produces the beams and has a collimator that helps to shape the beams as they exit the linac. It is very common for two or more beams to be used, each of which is delivered from different directions around the area of the tumor or the site of tumor resection. Often, in planning the delivery of the radiation, the beams are directed so that they will intersect at the tumor site, thereby focusing the highest dose of radiation at the most critical area. In this manner, the normal tissues surrounding the target are exposed to lower amounts of radiation. At the same time, the exact target site receives a more precise and accurately delivered dose, since the sum of the treatment beams are greatest at the directed tumor target. The tumor target volume is the region delineated by the radiation oncologist using CT scans (or other imaging methods such as ultrasound or MRI) of the patient. The tumor target volume and radiation dose prescription parameters are entered into a treatment planning computer. Treatment planning software (TPS) then produces a plan showing how many beams are needed to achieve the radiation oncologist's prescription dose, as well as the size and shape of each beam.

Historically, EBRT is practiced by dividing the total radiation dose into a series of smaller more tolerable doses which are delivered to the patient sequentially. Dosage is typically limited by the tolerance of normal tissues surrounding the site to be treated. Hence, often, the radiation therapy is continued until side effects become intolerable to the patient. The target volume, in which it is desired to deliver essentially 100% of the prescribed radiation dose, has historically been defined as the tumor (the gross tumor volume, or GTV) plus a surrounding volume of tissue margin that may harbor remaining microscopic tumor cells (the clinical target volume, or CTV). Another margin of surrounding normal tissue is added to the CTV to account for errors in positioning of the patient for therapy and movement of the tumor site both during a fraction and between fractions.

In the treatment of breast cancer, the complete course of EBRT is divided (fractionated) into numerous small, discrete treatments each of which is referred to as a "fraction". A typical prescribed dose of 60 Gray (Gy) is fractionated into 30 daily treatments of 2 Gy per day. During a fraction, the treatment beam may be "on" for ~1 minute. Thus, to achieve the full treatment dose, the radiation therapy is typically delivered 5 days per week over a 6 week period. In the treatment of breast, lung, chest and upper abdominal (e.g. pancreatic) cancers the delivery of radiation therapy must take into consideration the changes in tissue position during respirations which may alter the position of the target tissue.

Another common procedure in which EBRT is used is whole breast radiation, typically used as a radiation therapy regimen following surgical lumpectomy as treatment for breast cancer. In this form of therapy, the entire breast is irradiated multiple times in small dose fractions over a course of treatment that typically lasts about 1-2 months. In addition to these whole breast doses, most patients receive an additional "boost" dose that is given to the area immediately surrounding the lumpectomy cavity, as this region is suspected to be of higher risk of recurrence. Often there is difficulty and uncertainty in identifying the exact tissue location of this post-lumpectomy tissue region. As a result of this uncertainty, larger tissue volumes than would otherwise be necessary are defined for boost treatment to ensure that the correct "high risk" target tissue indeed receives the boost dose. In addition, as the boost target is smaller than the whole breast that was treated, the actual "targeted" boost tissue volume is smaller than the whole breast target and can be more difficult to specifically target or define for treatment.

In the last few years, the treatment planning software and linear accelerator technology have dramatically improved in their ability to shape the radiation therapy beams to better avoid nearby sensitive structures (also known as "organs at risk" or non-target tissues). The latest treatment planning software allows the radiation oncologist and medical physicist to define the volume of tissue to be treated using CT scans and provide therapy constraints (e.g., minimum radiation dose inside the target volume, maximum radiation dose to structures nearby target volume). The software then automatically computes the beam angles and shapes in a process called inverse treatment planning. This process can be even further refined using a technique called Intensity Modulated Radiation Therapy (IMRT) which shapes the beam of radiation. Another feature of the newer linear accelerators is a type of radiographic (and/or ultrasonic) imaging that is used to better position the patient and his/her tumor for more accurate targeting of the treatment beams. This latter method is called Image Guided Radiation Therapy. or IGRT.

Both IMRT and IGRT techniques use numerous, smaller and more precisely shaped beams that intersect at the target volume. IGR differs from IMRT in at least one important aspect—imaging prior to each fraction is used to reduce positioning errors and make sure the treatment beam is properly targeted. Typically, IGRT uses bony anatomy (e.g., pelvic bones for prostate patients) for radiographic targeting and soft tissue interfaces (e.g., prostatic capsule and bladder wall) for ultrasound targeting. Rarely, implanted radio-opaque markers (e.g., VISICOIL) have been used to facilitate targeting for IGRT. However, using a single marker device that defines in a 3 dimensional/volumetric manner the limits or margins of treatment has not yet been accomplished. In the treatment of breast cancer specifically, some clinicians have attempted to help delineate the margins of the lumpectomy cavity by using radio-opaque markers such as surgical clips placed at the time of surgery. This, in theory, may help the radiation oncologist in treatment planning, however, often these clips are inaccurate in their placement, have a tendency to migrate postoperatively (e.g., due to their mobility and other healing and scarring issues), and may be confused with other surgical clips used for haemostatic control during surgery. Tissue changes and scarring can markedly affect the position of these clips, thus leading to the possibility of inaccurate targeting of the radiation. In addition, these markers have not been used with significant success for targeting in the newer delivery methods, such as for each fraction or each beam of every fraction as is done in IGRT.

IMRT uses a special type of collimator, a multi-leaf collimator (MLC) that changes the shape of the beam during each fraction to modulate or "sculpt" the radiation dose to more closely fit the actual target volume shape in three dimensions. Linear accelerators equipped with MLCs can control the size and shape of the beam to within a few millimeters accuracy. However, to best take advantage of their precision, the tissue target needs to be accurately defined in 3 dimensions.

IGRT is a relatively new option on linear accelerators, however many new linacs are available today that have on-board imaging capability via mega-voltage (MV) or kilo-voltage (KV) x-rays/fluoroscopy. The on-board imaging capability can also be retrofitted to existing equipment. On-board imaging is a technical capability that has been introduced into the newest linac product lines by major manufacturers of linear accelerators (e.g., Varian Medical Systems, Elekta, Tomotherapy, Accuray and Siemens). While the technology made by these companies provides the possibility of performing better targeting for external beam radiation therapy, the targets (e.g., bony anatomy) are inadequate in order to achieve a precise and accurate target region for precision treatment of a specific tissue region, often because of inaccuracies associated with correlating bony anatomy to the adjacent soft tissue target region.

As described above, targeting the external beam radiation therapy accurately requires one to point out the target using markers known as "fiducials." These fiducial markers have different radiographic properties than that of the surrounding tissue (e.g., bone, and sot tissue). To date, this has been accomplished using radio-opaque markers (e.g., permanently implanted foreign bodies). Alternatively, Patrick and Stubbs described a device and method for shaping and targeting EBRT using a temporarily implanted balloon catheter (U.S. Pat. No. 7,524,274). This device and method required implantation of a foreign body whose removal necessitated a second medical/surgical procedure. There is clinical evidence suggesting that the implantation and irradiation of an area of the breast surrounding an implanted balloon can result in long-standing complications such as persistent seroma (collection of fluid within the breast that may become infected). There are a number of clinical difficulties that preclude use of a balloon-type device as a realistic/good option to define a tissue target for radiation. For example, a balloon device may interfere with the EBRT treatment since the balloon and its contents may affect the transmission of the EBRT, and therefore may affect the dose of radiation reaching the target tissue. In addition, the balloon may inhibit tissue growth back into the cavity during the healing process, which can lead to irregular and unsightly scarring, which is particularly undesirable following breast surgery for cancer. The balloon can be uncomfortable to the patient during the course of treatment, and thus, use of a balloon-type device for targeting radiation therapy has not been useful in the clinical domain.

Hence, the need exists for a better fiducial marker device and method for more accurately defining the target tissue volume and providing an imageable target for the external beam treatments, without requiring subsequent removal.

SUMMARY

The invention described herein uses implantable devices that can allow for more accurate targeting of external beam radiation to the region of tissue that is to be treated. The devices provide a 3-dimensional target or group of targets that is used to focus the radiation therapy treatment beams directly onto the targeted tissue—for example, the tissue surrounding a tumor resection cavity. The device may be formed of an absorbable material that is implanted intraoperatively during the same surgical procedure as the tumor resection and requires no second procedure to remove (it is resorbed in situ in the patient's body).

In a first aspect, an implantable fiducial tissue marker device is provided for placement in a soft tissue site through an open surgical incision. The device includes a bioabsorbable body formed whose outer regions define a peripheral boundary of the marker device. A plurality of visualization markers are secured to the body so that visualization of the marker device using medical imaging equipment will indicate the 3-dimensional location of the tissue site. The device is also conformable to the adjacent soft tissue and its peripheral boundary is able to be penetrated by adjacent soft tissue during its use.

In specific embodiments, the bioabsorbable body is in the shape of a spiral where the spiral has a longitudinal axis and turns of the spiral are spaced apart from each other in a direction along the longitudinal axis. The peripheral boundary of the device can have a shape selected from the group consisting of spherical, scalene ellipsoid, prolate spheroid, and oblate spheroid shape. The device can also have a north polar region and a south polar region at opposed ends of the longitudinal axis. A strut can further be connected between the north polar region and the south polar region. The strut can include a sliding element to allow the spiral body to be compressed in the manner of a spring.

Visualization markers can be attached to the body in the north polar region and/or the south polar region. A plurality of visualization markers can also be attached to the body about an equatorial region of the substantially spheroid device. In one embodiment, at least four visualization markers are attached to the body about its equatorial region. At least some of the visualization markers can be radio-opaque clips. The radio-opaque clips can be attached to the body using preformed holes in the body into which the clips can be pressed and attached.

In a further aspect, a method for fabrication of a tissue marker device is provided. The device can be fabricated using injection molding to form a body made of a bioabsorbable polymer in a planar configuration. The body can be heat formed so that the body is reconfigured from a planar configuration to a three dimensional configuration.

In specific embodiments, fabrication of the device can include forming pockets or through-holes in the body during injection molding and attaching visualization markers to the pockets or through-holes. The injection molded body can include north and south polar regions, with each polar region including a polar extension that is directed toward an interior of the device. Fabrication can further include connecting a strut to the polar extensions. The strut can be slideably connected to at least one of the polar extensions. Also, two or more separate parts can be connected to achieve a finished product.

In a still further aspect, an implantable tissue marker device is provided to be placed in a soft tissue site through a surgical incision. The device can include a bioabsorbable body in the form of a spiral and defining a spheroid shape for the device, the spiral having a longitudinal axis and turns of the spiral being spaced apart from each other in a direction along the longitudinal axis. A plurality of markers can be disposed on the body, the markers being visualizable by a radiographic imaging device. The turns of the spiral are sufficiently spaced apart to form gaps that allow soft tissue to infiltrate between the turns and to allow flexibility in the device along the longitudinal axis in the manner of a spring.

In specific embodiments, the device can have a spring constant in the direction of the longitudinal axis between about 5 and 50 grams per millimeter. The bioabsorbable body can include opposed polar regions along the longitudinal axis. Markers can be placed in each of the polar regions. A plurality of markers can also be placed along an equatorial region of the body. In one embodiment, at least four markers are placed along the equatorial region.

BRIEF DESCRIPTION OF THE DRAWINGS

The invention will be more fully understood from the following detailed description taken in conjunction with the accompanying drawings.

DETAILED DESCRIPTION

The invention described herein uses implantable devices that can allow for more accurate targeting of external beam radiation to the region of tissue that is to be treated. The devices provide a 3-dimensional target or group of targets that is used to focus the radiation therapy treatment beams directly onto the targeted tissue—for example, the tissue surrounding a tumor resection cavity. The device may be formed of an absorbable material that is implanted intraoperatively during the same surgical procedure as the tumor resection and requires no second procedure to remove (it is resorbed in situ in the patient's body).

In one embodiment, the invention includes a spiral, bioabsorbable surgical implant 10 (illustrated in FIG. 1A in a spherical configuration and in FIG. 1B in an ellipsoid configuration) with at least one integral targeting marker component that is visible by means of clinical imaging (radiographic, ultrasonic, MRI, etc.). In many embodiments, the implant 10 has a relatively non-complex peripheral shape that can facilitate easy target delineation, such as spheres, ellipsoids, or cylinders. In this way, the implant (and/or the markers affixed thereto) can be visualized, and its contours (and thus the contours of the target tissue to be treated-typically marginal regions surrounding an excised tumor) can be readily determinable. Treatment can then be applied to the target tissue. The size and shape of the implant can be varied to correspond to the most common resection cavity sizes and shapes. The device may be flexible and may be in its predetermined shape before placement and although it may tend toward that predetermined shape after implantation, the implant is subject to the forces applied to it by the patient's tissue and hence its shape is able to deform and conform to the adjacent tissue as well. Similarly, the device may become integrated into the surrounding tissue as it is absorbed by the body, leaving the markers in proximity of the previously excised tumor for future clinical tracking. The device can be sized as needed for a particular surgery, however, preferred sizes range from about 2 cm to about 6 cm in longest diameter.

Figure 1A:
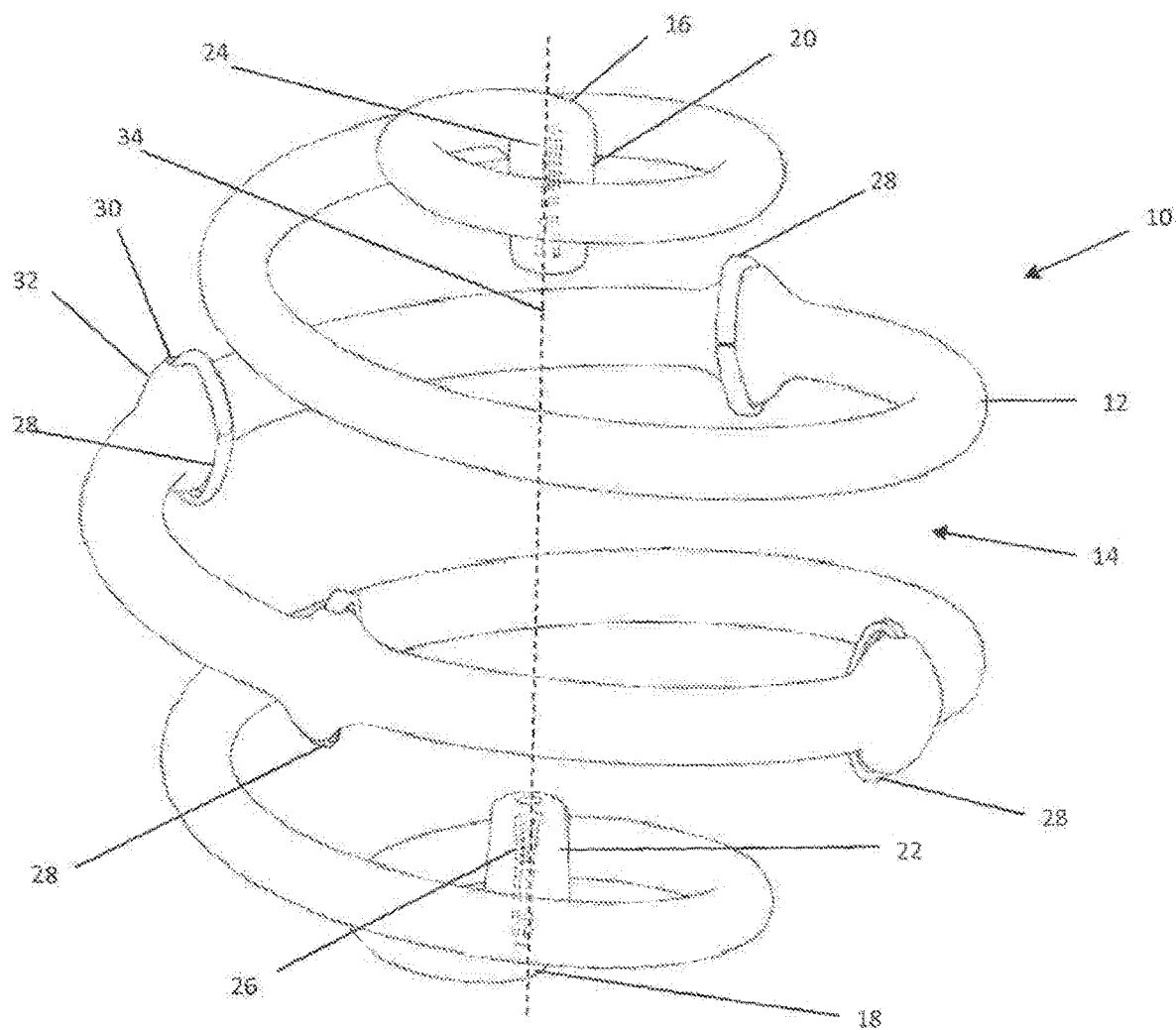
FIGS. 1A and B illustrate a spiral implant device of the invention.
Figure 1B:
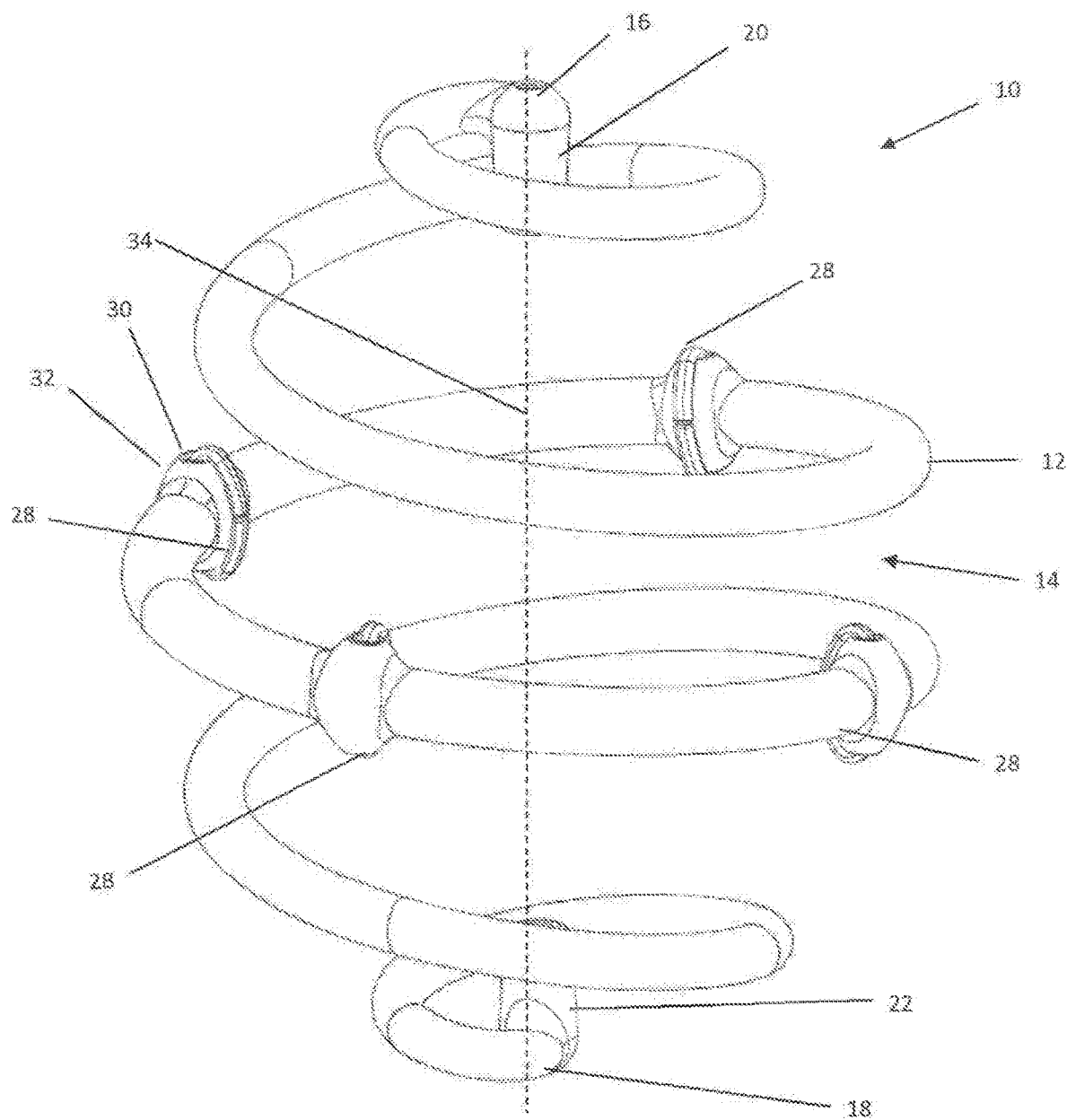

As illustrated in FIGS. 1A and 1B, the surgical implant 10 of the invention is formed as a spiral. The spiral nature can permit the implant 10 to be more flexible than it otherwise might be. For example, the implant 10 can flex along its axis 34 in length in the manner of an extension or compression spring or bend along its axis 34 in the manner of bendable coil spring. In addition, the lack of continuous walls can allow the implant to flex in directions other than along its axis. Such flexibility can allow for the target tissue, and the cavity into which the implant 10 is placed, to flex as the patient moves, making the implant more comfortable for the patient. In addition, the open nature of the spiral can allow tissue growth and insinuation into the cavity which may reduce the incidence or effects of seroma, and in some instances may be able to reduce the volume of the target to be irradiated.

The shape of the illustrated implant 10 in FIG. 1A is spherical, however, the implant could also be made in other shapes, such as a football-shaped ellipsoid (illustrated in FIG. 1B) or cylindrical. As used herein, the term "spheroid" is expressly intended to include both spherical and ellipsoid shapes for the implant 10—as such, both the embodiments of FIG. 1A and FIG. 1B are spheroid. The choice of shape may depend on the shape and nature of the cavity into which the implant 10 is being placed. In the case of a lumpectomy cavity commonly related to breast cancer, a relatively spherical shape is a common choice.

While the implant 10 could have any shape, regular shapes that are readily modeled by external radiation beam treatment devices are preferred. Such shapes can include spherical, scalene ellipsoid, prolate spheroid, and oblate spheroid shapes. Again, the use of the term "spheroid" herein is intended to include all of these spherical and ellipsoid shapes. Other regular shapes such as cylinders or squares could also be used, however, sharp corners might make it more difficult to shape radiation doses to the target tissue. In general, the implant 10 can have polar regions with an open framework extending between the polar regions. Such an open framework would include a body 12 that provides sufficient stability to mark the boundaries of a tumor resection cavity, while having sufficient gaps 14 in the body to allow tissue around the cavity to infiltrate the device. In this illustrated embodiment, the shape of the implant 10 is created by a continuous or one-piece body 12 that is formed into a spiral having gaps 14 between the turns of the spiral, the overall spiral having a spherical shape with polar regions 16, 18. In each polar region 16, 18, there is an extending portion 20, 22, which, in this embodiment, extends inward toward the center of the spherical shape.

In addition, the open framework can be designed to provide specific levels of flexibility. As noted elsewhere herein, the illustrated spiral design acts as a spring. By varying the rigidity of the material making up the body 12, and/or by varying the thickness of body 12, a spring constant for the device 10 can be varied to achieve a desired flexibility. That is, by design the spring constant may provide a certain amount of force in order to keep the markers in their position along the margins of the cavity, but allow sufficient flexibility for patient comfort and to minimize scarring, therefore the device 10 can be optimized for its intended purposes. Preferred embodiments for use in treating breast cancer include those having a spring constant (denoted as "k", in units of grams/mm) between about 5 and 15 grams per millimeter axial deflection for the 4 cm diameter devices (more preferably 8-12 g/mm), between about 10 and 25 g/mm axial deflection for the 3 cm diameter devices (more preferably 15-20 g/mm), and between about 25 and 70 grams/mm axial deflection for the 2 cm devices (more preferably 30-50 g/mm). The inventors have discovered that it can be beneficial to have higher k values for smaller diameter devices.

Typical sizes of the device range from 2-6 cm in equatorial diameter and 2-8 cm in length. It is useful for the clinician to have a range of product diameters and lengths to choose from to provide the optimal configuration for a given patient.

The implant 10 is preferably able to be visualized on a medical imaging apparatus so that it can be used for targeting therapy. In the illustrated embodiment, visualization characteristics may be enhanced by providing by visualization markers in the form of radio-opaque clips 24, 26, 28 that provide high contrast visibility on imaging devices. In the illustrated configuration, a first clip 24 is provided at the "north pole", a second clip 26 is provided at the "south pole", and four clips 28 are distributed substantially around the equatorial region of the spherical implant 10. This clip array permits a specific outlining, or in other words a characterization of the extent of the borders of the tissue cavity in all 3 dimensions, and in this embodiment, the xy, zy and xz planes. More or fewer clips can be used to provide more detailed or less detailed tissue site identification, as needed. Given the flexibility and shape of implant 10 as described and illustrated, clips are preferentially provided at the two poles and also in some number distributed substantially about the equator, or elsewhere along its spiral length. In this manner, even where the spherical implant flexes in vivo, or the tissue around the cavity moves or flows, the 3 dimensional shape of the tissue region can be identified, based on the location of the clips. It is worth noting that, with currently available high resolution imaging systems, including CT, mammography, MRI, and ultrasound, the presence of the clips may not be necessary to image the implant and hence image the surrounding soft tissue. The mere presence of the bioabsorbable body, which need not contain air gaps in the body material, can in some cases, be sufficient to delineate or demarcate the desired tissue location.

Figure 7:
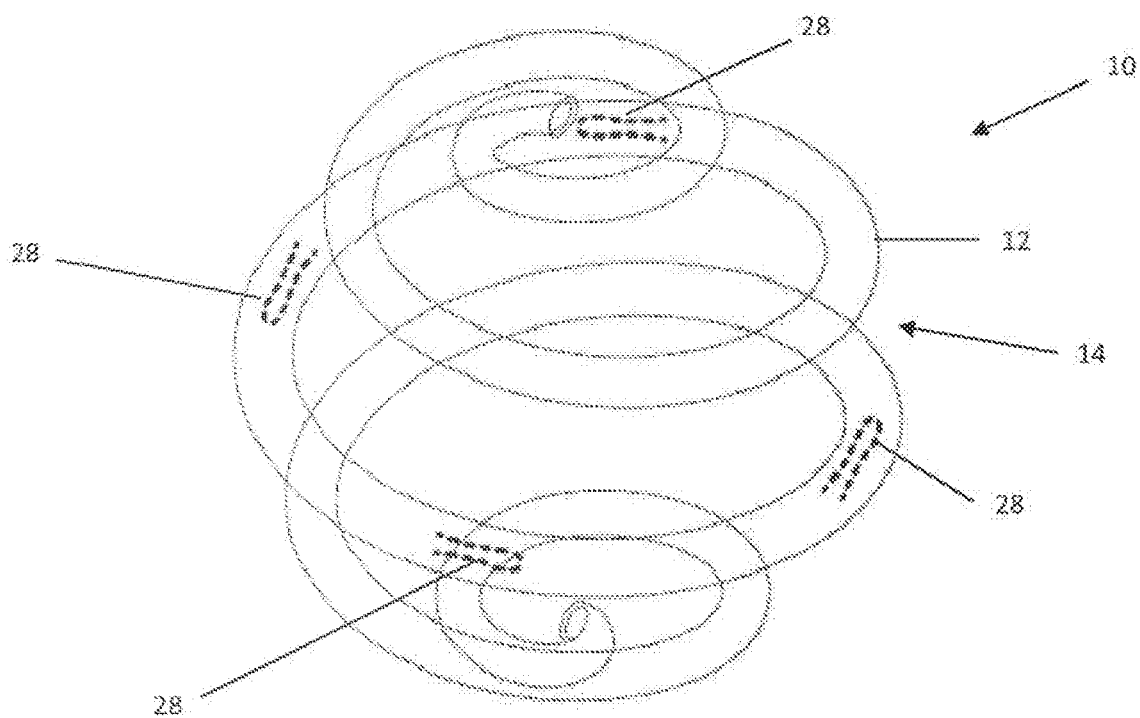
FIG. 7 illustrates an alternate embodiment of a spiral implant device of the invention.

As illustrated, each of the north and south pole clips 24 and 26 is located within the respective polar region extension 20, 22. Each of the clips is secured to the body material. In this embodiment, the polar clip is configured as a wire element that is folded onto itself, with the wire ends slightly flared prior to assembly. During assembly the clip is inserted into a cylindrical hole in the polar region. The flared ends of the clip serve as a unidirectional gripping element that prevents the polar clip from backing out of the hole once it is installed. The equatorial clips may be secured to body 12 using pockets or through-holes 30 created in regions 32 that exist for the purpose of providing the clips with a location to provide secure attachment. These equatorial clips 28, also made from metal wire can be attached by providing that the middle portion of the clip resides within the hole 30, and the end portions of the clip curve around the region 32, as illustrated, to fix them securely to the body 12 in the shape of a "D". This D shape facilitates the differentiation of these marker elements from the polar clips and from conventional haemostatic clips that may be used to control bleeding during the surgical procedure. In an alternate method of securing the clips, as can be seen in FIG. 7, the peripheral clips 28 may be placed in a lumen of a long spiral segment 12 of bioabsorbable tubing. The clips can be made from any biocompatible, radio-opaque material, such as titanium, stainless steel, gold or composite polymer materials (e.g., made with carbon or Barium Sulfate) having the desired visualization characteristics.

As noted above, the bioabsorbable body 12 itself may have visualization properties in addition to or in place of the clips 24, 26, 28. That is, the characteristics of the body material, or a coating on the body, may be chosen so that the body itself may be visualized on an imaging device and used for targeting. In particular, the body 12 may have radiodensity (or magnetic spin recovery when using MRI) that is different from the tissue surrounding the cavity into which the implant 10 is placed for the purpose of making the body 12 visible on an imaging device. For example, breast tissue can present values ranging from −140 to 50 on the Hounsfield scale-a linear transformation of the original linear attenuation coefficient measurement to one in which the radiodensity of distilled water at standard pressure and temperature ("STP") is defined to have a Hounsfield number of zero, while the radiodensity of air at STP is defined to have a Hounsfield number of −1000. Details for creating this contrast in an implantable device can be found in published U.S. patent application no. 2011-0004094 A1, filed on May 28, 2010 and entitled Bioabsorbable Target for Diagnostic or Therapeutic Procedure, which is hereby incorporated by reference. The density of the body 12, however, should not be so high as to impart significant attenuation of the radiation beams or imaging artifact, which may result in clinically compromised target delineation or altering the dose delivered by a clinically significant amount. Where clips or other markers are used, the density of the body 12 may in some cases be indistinguishable from that of the surrounding tissue for visualization and treatment purposes. In addition, the body 12 material and/or the clips may have a roughened or faceted surface finish to enhance the ultrasound imaging ability of the visualization device.

Various materials that could be used to construct body 12 include known bioabsorbable materials such as polyglycolic acid (PGA, e.g., Dexon, Davis & Geck); polyglactin material (VICRYL, Ethicon); poliglecaprone (MONOCRYL, Ethicon); and synthetic absorbable lactomer 9-1 (POLYSORB, United States Surgical Corporation) and polydioxanone. Other materials include moldable bioabsorbable materials such as poly lactic acid (PLA), including Poly L-lactic acid (PLLA) and various PLA/PGA blends. These blends can include caprolactone, DL lactide, L lactide, glycolide and various copolymers or blends thereof. Mixtures of any of the aforementioned materials can also be used, as required. The materials can be modified, by cross-linking, surface texturing, or blended with one another to control degradation rates over varying lengths of time, after which they are substantially or completely resorbed. Another manner in which degradation rates can be altered is by subjecting them to additional radiation in the dose ranges typically used for radiation sterilization. For example, subjecting the device to e-beam radiation in the dose range of 25 to 40 kiloGray (kGy) is typical for an adequate, validated sterilization cycle. However, subjecting the device to an additional 25 to 75 kGy can be useful to accelerate the in-situ degradation rate without significantly adversely affecting the functional short-term mechanical properties of the device. In embodiments that are used for radiation therapy targeting, the mechanical properties of body 12 are maintained for a long enough for treatment to take place. In some cases, the body 12 lasts long enough for tissue to infiltrate the cavity such that the position of the visualization markers is fixed within the tissue. Also, the material is preferably rigid enough for the overall effect of the spiral shape to behave in a resiliently deformable manner after implantation.

A cross sectional shape of the body 12 may also be selected to achieve the desired spring constant and absorbance parameters. In general, body 12 may have a cross section that is circular, oval, ovoid, cruciform, or rectangular. Other shapes can also be used.

Figure 2:
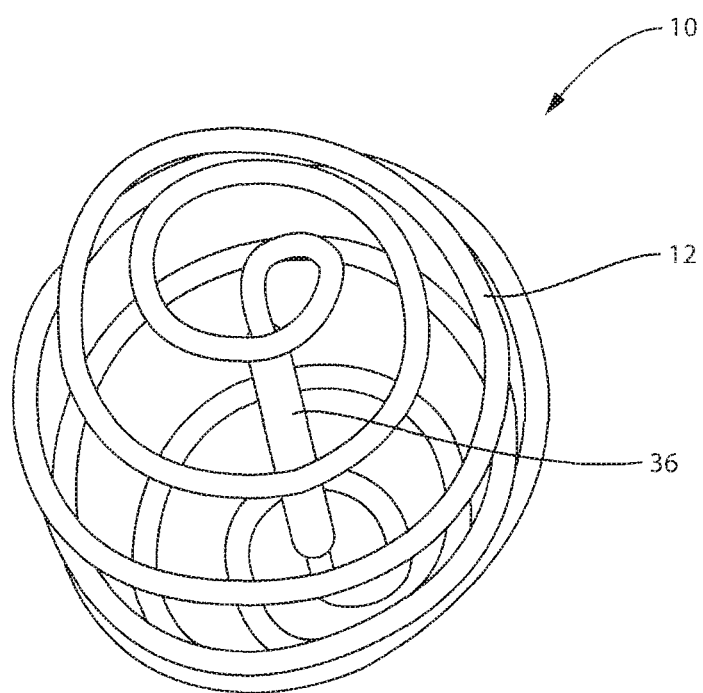
FIG. 2 illustrates a spiral implant device of the invention having a central strut.
Figure 3:
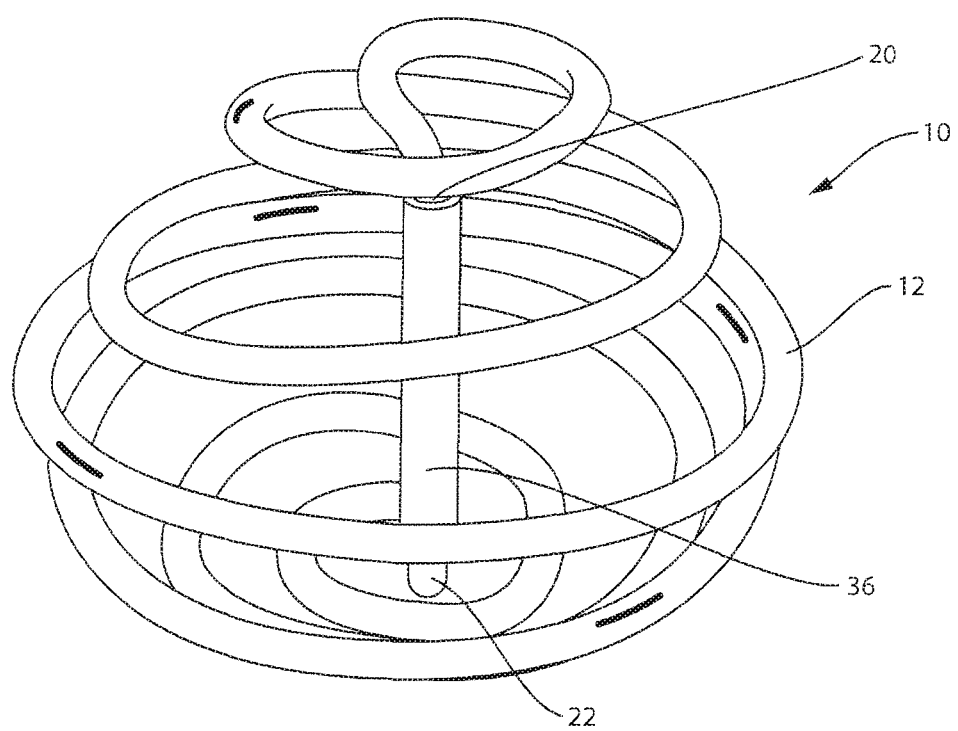
FIG. 3 illustrates a spiral implant device of the invention having a central strut, with marker clips secured within the spiral body.

As illustrated in FIGS. 2 and 3, the implant 10 may also have a strut 36 extending in the direction of its longitudinal axis 34. In particular, the strut 36 can be connected between the north and south polar extensions 20, 22. In a preferred embodiment, the strut 36 provides structural support, but also allows some translation of at least one polar region toward or away from the other polar region with respect to an unflexed position of the spiral body 12. In many situations in use, the spiral body 12 will flex in the manner of a spring and particularly in compression. Strut 36 allows compression along the longitudinal axis, but may also provide a stop to prevent over compression of the spiral body 12.

In one embodiment, the strut 36 is a tubular element that fits over each of extensions 20, 22 and maintains a fixed relationship with one extension while sliding with respect to the other extension. This configuration would allow the spiral body 12 to be compressed until an edge of the tubular strut 36 contacted one of the polar regions 16, 18 which would act as a stop. In another embodiment, the strut 36 could slide with respect to each of the extensions 20, 22. In a still further embodiment, the strut 36 could comprise two overlapping tubes that slide with respect to each other in the longitudinal direction and opposed ends of such a strut could be fixed to the polar extensions 20, 22. In a non-sliding embodiment, the strut 36 could be fixed to both extensions 20, 22 with no internal sliding.

Figure 4A:
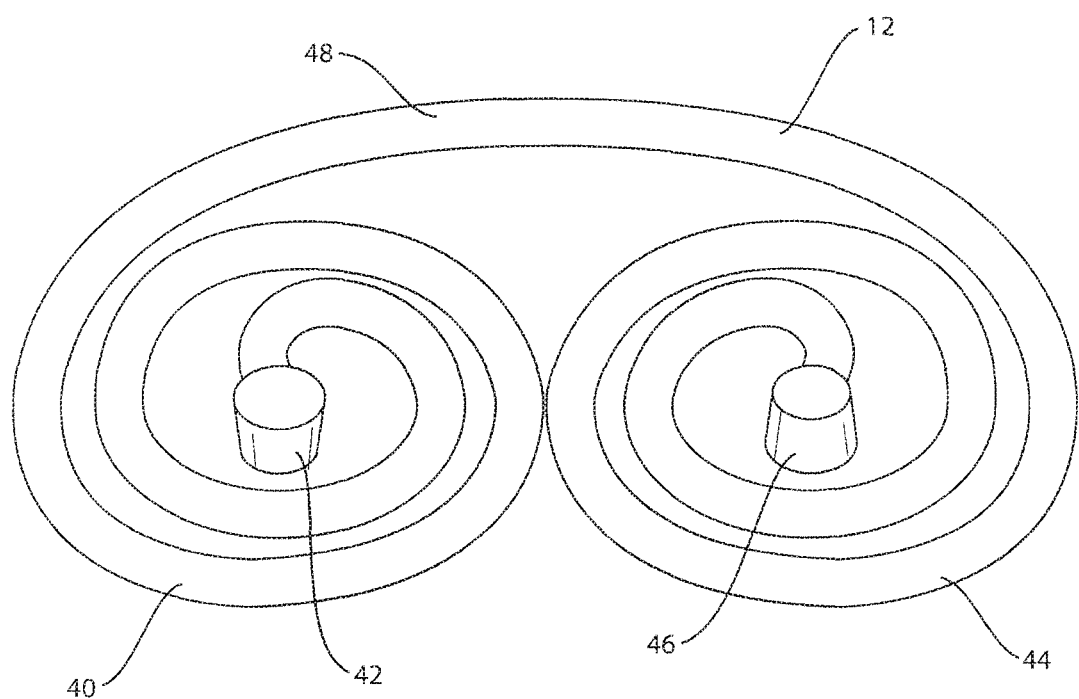
FIGS. 4A and B illustrate stages of fabrication for a spiral implant device of the invention.
Figure 4B:
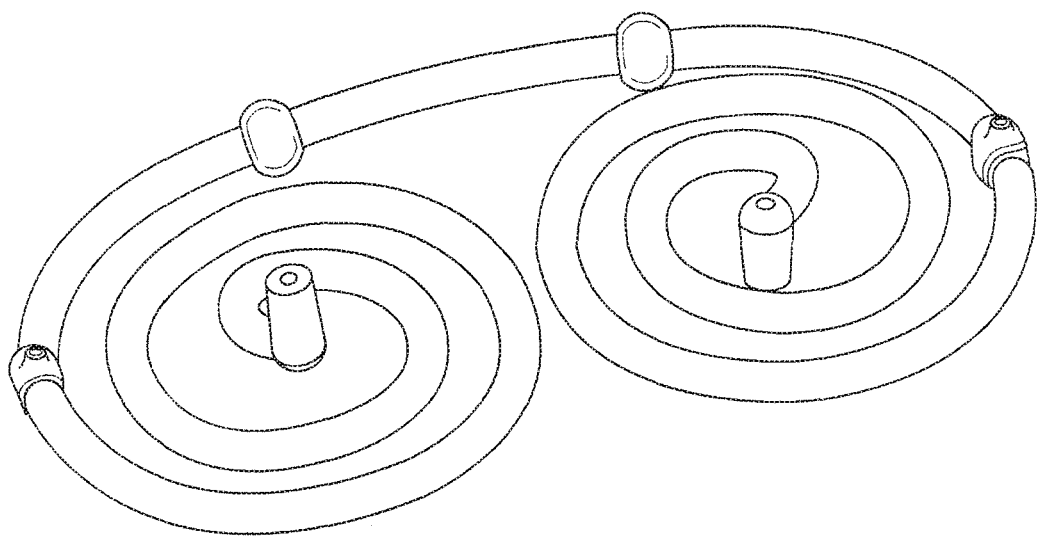
Figure 5:
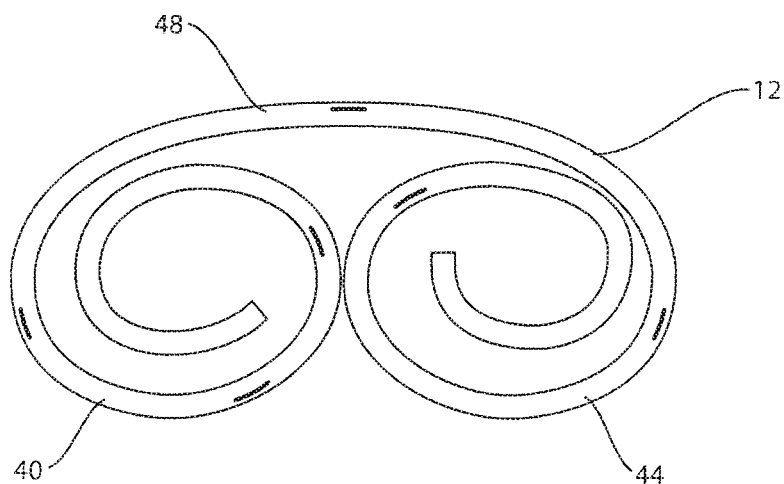
FIG. 5 illustrates a stage of fabrication for a spiral implant device of the invention.

The present inventors have also developed a preferred fabrication method for forming the body 12. In a fabrication step, illustrated in FIGS. 4 and 5, body 12 is formed into two substantially planar, opposed, and connected spirals. Body 12 could be extruded and then heat-formed as shown in FIG. 5 (the shaping of a thermoplastic material by heating it and causing a permanent deformation (such as bending) that remains after the material cools) into the desired shapes described above, however, such handling of bioabsorbable is difficult and repeatability in forming the shapes can be challenging. In a preferred embodiment, this first step is carried out by injection molding as shown in the spiral forms of FIGS. 4AB and C. This shape can be molded from a simple two part mold without the need for side pulls, which allows for repeatability yet modest tooling costs. In addition, the molded part allows for more surface detail, for example at the two ends of the part—rounded ends with pockets for visualization markers or fabrication fixtures may be incorporated into the design, as illustrated for example in FIG. 4A. Pockets for additional visualization markers can be molded along the length of the body at appropriate intervals, as shown in FIG. 4I.

The entire body 12 may at this stage be substantially planar to facilitate injection molding. When we say substantially planar we mean of a configuration that is able to be injection molded without the need for side pulls, or that can be die cut from a sheet form of the body material. Visualization markers may also be attached to body 12 at this stage where the body is substantially planar, as shown in FIG. 4C, which is conducive to automated assembly methods.

In the embodiment of FIG. 4, left spiral 40 includes a north polar extension 42, while opposed right spiral 44 includes a south polar extension 46. A connecting segment 48 connects the two opposed spirals.

Figure 6:
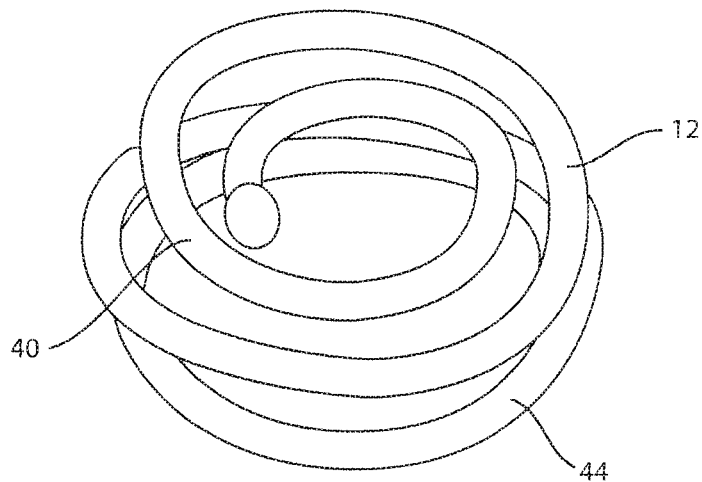
FIG. 6 illustrates a further stage of fabrication for a spiral implant device of the invention.

FIG. 5 illustrates a similar embodiment to FIG. 4, but lacking polar extensions, which could be heat-formed later, or omitted completely—especially if a central strut is not desired. A subsequent step in a fabrication process results in a device that is illustrated in FIG. 6, where the configuration of FIG. 5 has been heat-formed so that one spiral 40 is located above the other spiral 44 so that the spirals share a common longitudinal or central axis. For the embodiment of FIG. 5, either spiral could go over the other. For the embodiment of FIG. 4, however, having polar extensions 42, 46 that have a directional element, the left spiral 40 preferably would be placed on top of the right spiral 44 so that the polar extensions extend toward each other—that is, toward the center of the finished spiral implant.

During the heat-forming process the centers of the overlapping spirals 40, 44 can be reformed, (e.g., over a mandrel) so that body 12 takes the general shape of a sphere. The final shape of the final implant can be determined during this heat forming step. For example, heat forming the centers to project out of plane less than the full radius distance of a sphere shape will result in a flattened sphere. Heat forming beyond the full radius distance will elongate the sphere to a football shape as shown in FIG. 1B. Forming one spiral side farther from the midline than the other will result in an egg shape. In embodiments in which the central strut is desired, the strut may next be added. To facilitate even and repeatable reforming, the body 12 may be placed around a spheroid forming mandrel and heated to form the final desired shape. To enhance fabrication consistency, the forming mandrel may have channels along its surface to hold the part in a given position during the heat-forming process.

FIG. 7 shows a device formed as shown in FIG. 6, with the addition of marker clips which are placed at desired locations along the central lumen of the body of the device. These marker clips may be placed in the lumen before or after final heat forming into the final spheroid spiral shape.

Figure 8A:
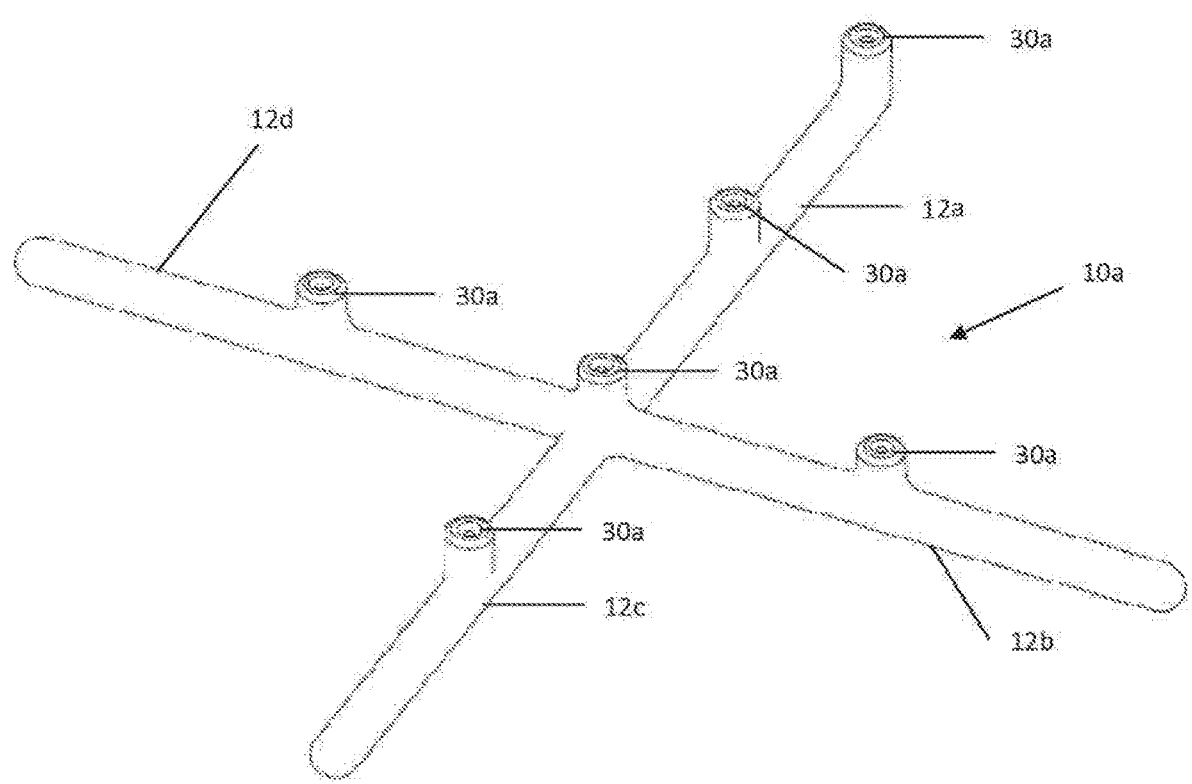
FIGS. 8A and B illustrate an additional embodiment of an implant device of the invention.
Figure 8B:
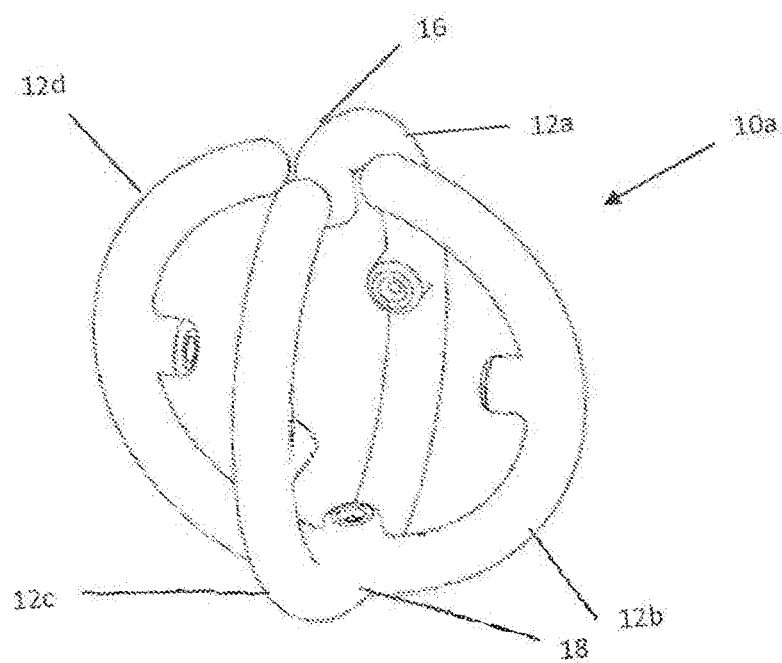

FIGS. 8 through 10 all describe alternate embodiments where the bioabsorbable marker component (e.g. body 12) is initially formed in a relatively planar configuration (e.g. for case of injection molding) and then the component is subsequently heat-formed into its final spheroid or other three dimensional configuration. Note that the embodiments have an open architecture to maximize the opportunity for tissue ingrowth, tissue movement, tissue approximation and/or fluid communication across the peripheral boundary of the marker device. The open architecture also allows for the passage of suture around a portion of the device by the clinician to help secure the device to adjacent tissue (e.g., chest wall) to further immobilize the device. The marker devices described herein comprise a resilient framework of bioabsorbable elements with locations for periodic secure attachment of radiodense marker elements (e.g., titanium wire) along the periphery of the device. The flexibility and conformability of the device allows for device deformation for increased comfort and conformance to the surrounding tissue in which the device is placed. When we use the term "peripheral boundary" of the marker device, we are referring not only to the boundary edge of the marker device itself but also to the "empty space" regions in between the portions of the marker device that are generally consistent with the perimeter of the device.

FIG. 8A shows an alternate embodiment of the device 10a where the bioabsorbable component is molded in a planar, cross-like configuration with a body having four branches. 12a. 12b, 12c, and 12d. Each branch includes a feature 30a for attaching a marker about an equator of the device, while one branch 12a includes at its end a feature 30a for attaching a north pole marker and the center of the cross includes a feature 30a for attaching a south pole marker. FIG. 811 shows the device after the component has been heat formed (e.g., around a spherical mandrel with recessed grooves) to generate a spherical device 10a having north and south polar regions 16, 18. Other shapes described herein could also be formed in this manner, as well as, shapes formed with more or fewer branches. In general, the number of branches will be based upon the width of the branches, the desired size of gaps between the branches in the finished device (and thus the device's "openness"), and the number of markers desired about the equator of the device.

Figure 9A:
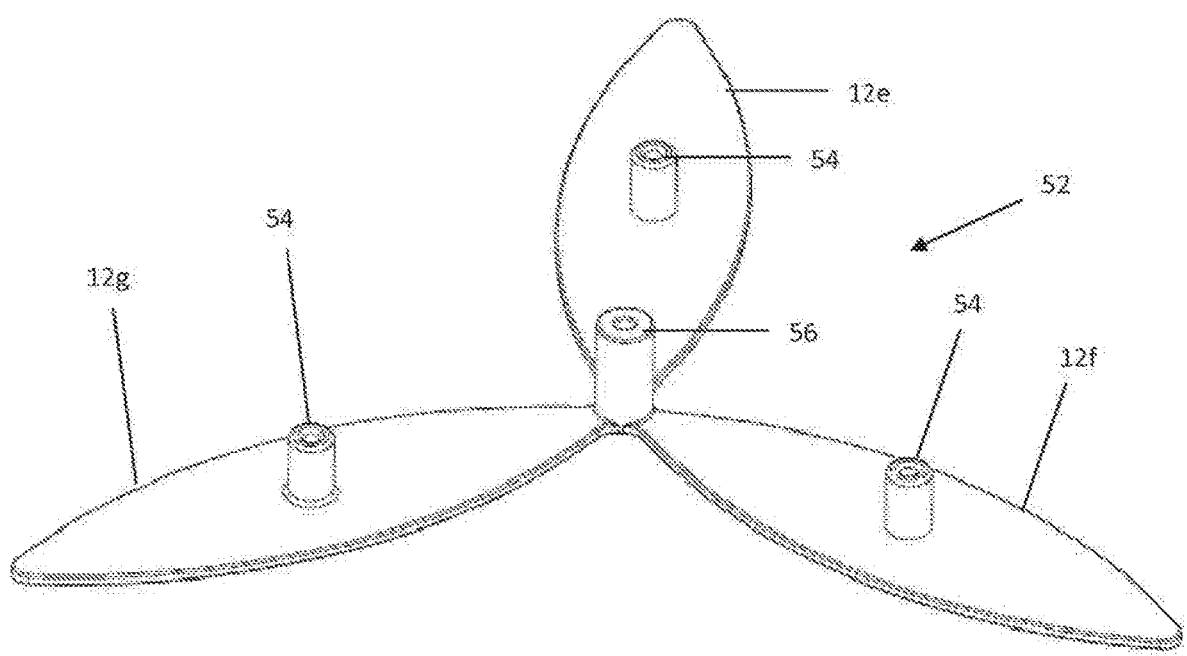
FIGS. 9A, B, C and D illustrate an additional embodiment of an implant device of the invention.
Figure 9B:
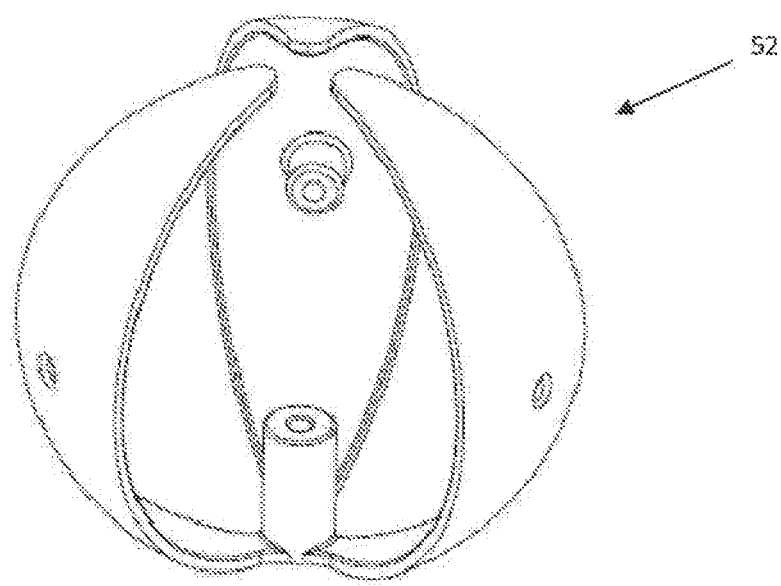
Figure 9C:
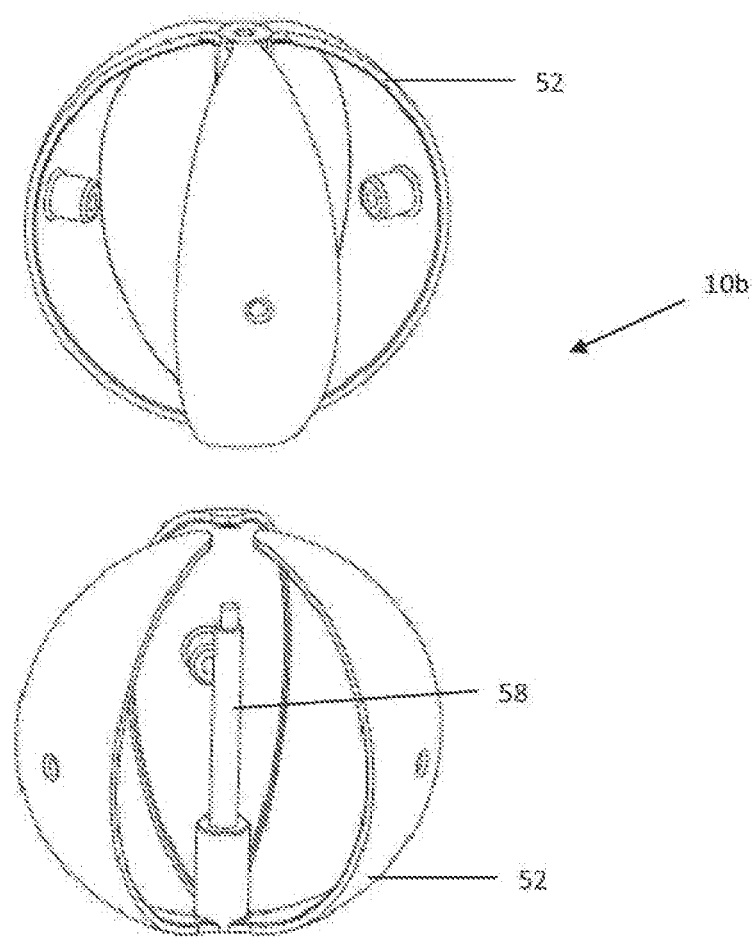
Figure 9D:
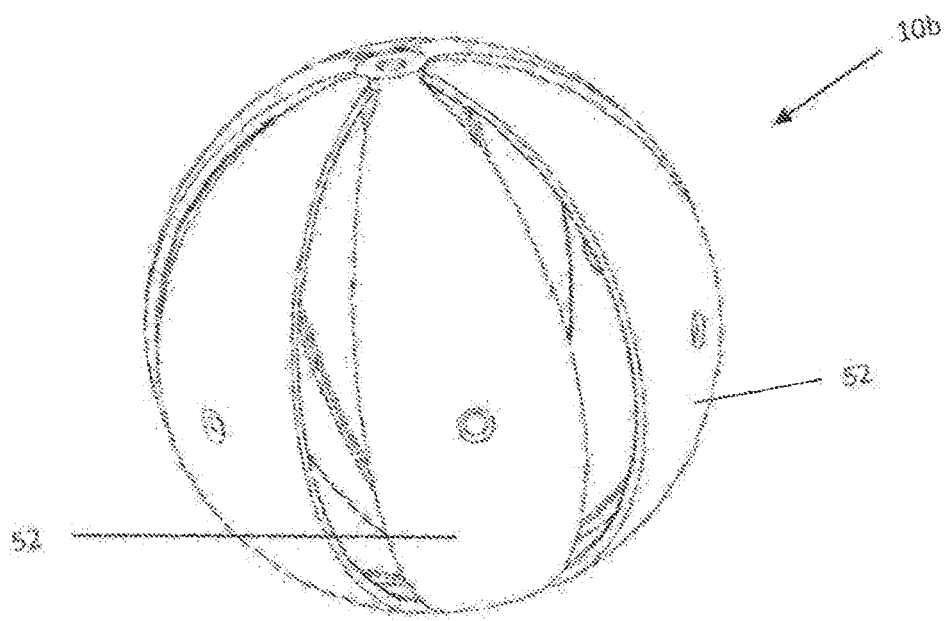

Another embodiment of the device is shown in FIGS. 9A through 9D. A first portion 52 of a bioabsorbable component 10b is molded in the form as shown in FIG. 9A having three petal-like branches 12e, 12f, and 12g. The three cylindrical protrusions 54 in the center of each petal-like element contain a radiopaque marker (not shown) such as a titanium wireform for use as equatorial markers. The central cylindrical protrusion 56 comprises a fastening means (e.g., press-fit or mating threads) for assembling the device and can also include a radiopaque marker (not shown). The component 52 can subsequently be heat-formed around a curved mandrel to create a component as illustrated in FIG. 913. A central axial extension 58 can be added to two portions 52 to create an assembled bioabsorbable device 10b as shown as FIG. 9C, which is the exploded view of the completed device that is shown in FIG. 9).

Figure 10A:
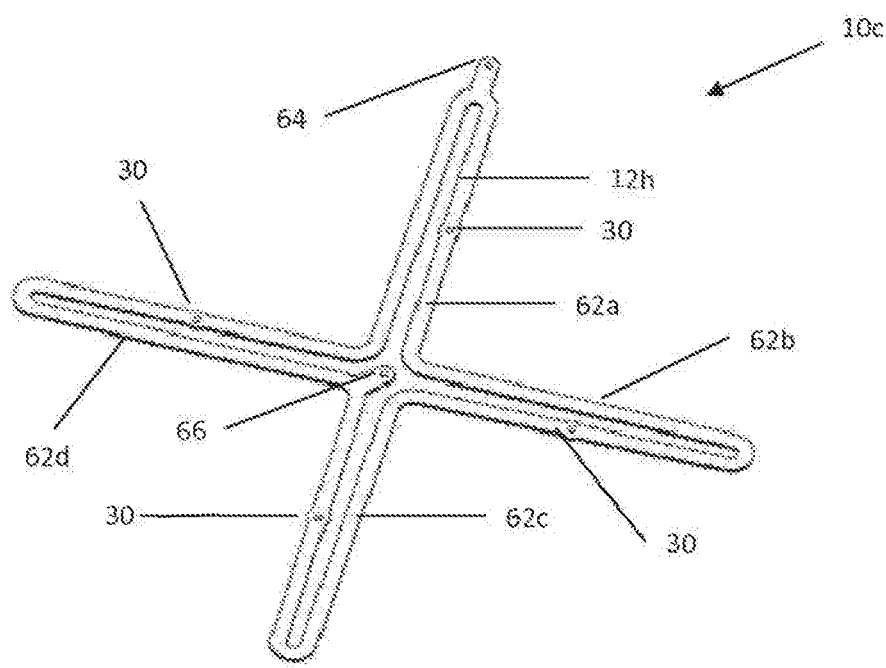
FIGS. 10A, B, C, and D illustrate an additional embodiment of an implant device of the invention.
Figure 10B:
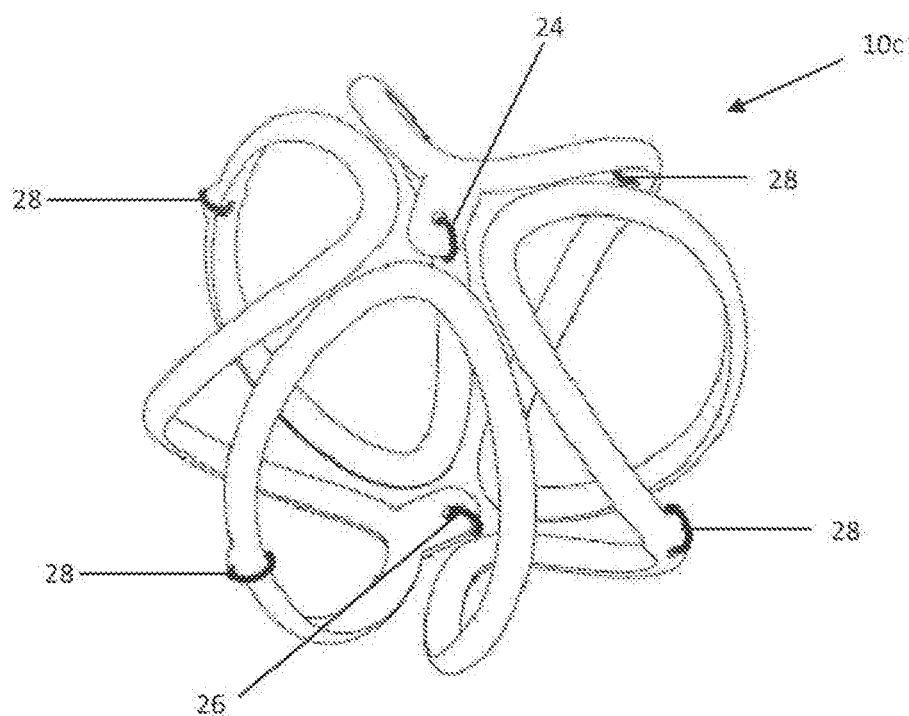
Figure 10C:
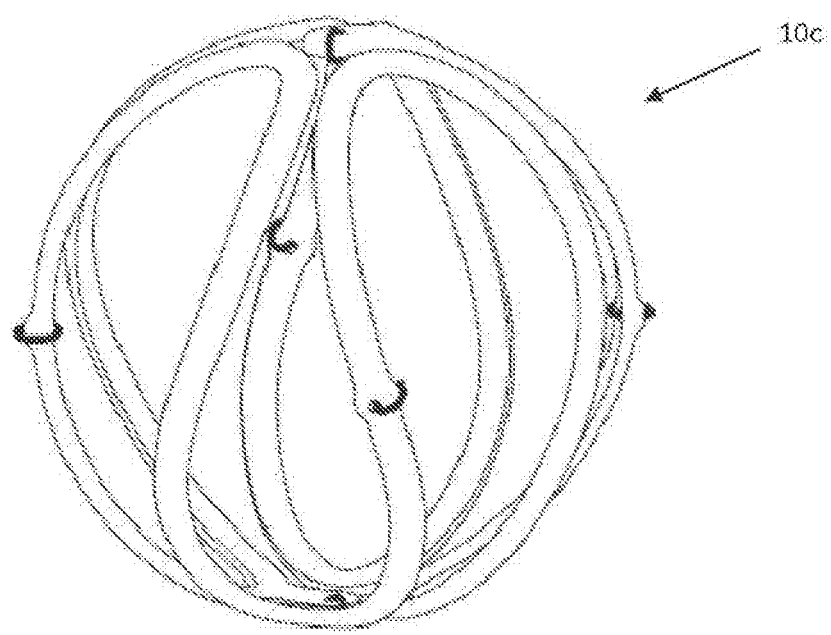
Figure 10D:
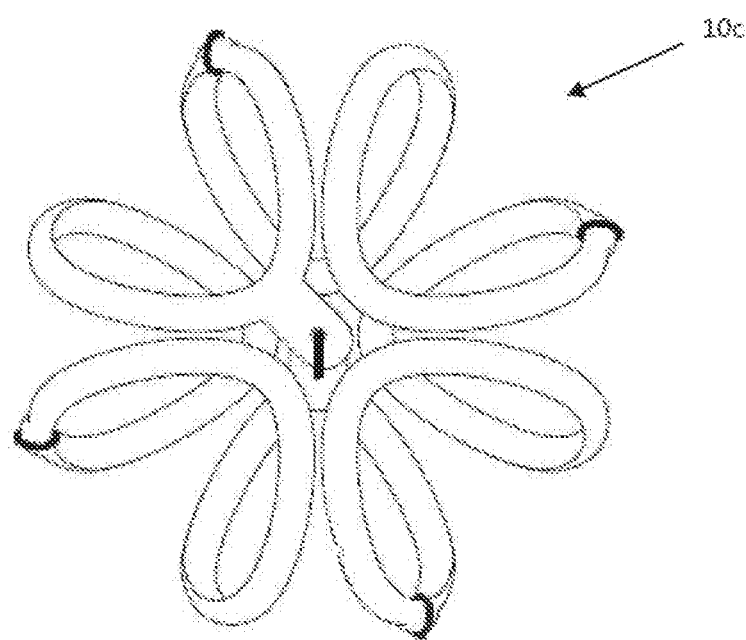

FIGS. 10A to 10D show yet another embodiment of the device 10c where the bioabsorbable component is molded in an alternating continuous filament 12h configuration forming four loops 62a-62d in the form of a cross with each loop being open towards the center. Each loop 62a-62d includes a feature 30 to allow placement of equatorial markers 28. Loop 62a includes a feature 64 for placement of a north polar marker 24, while a feature 66 for placement of a south polar marker 26 is located at the center of the device 10c between any two loops. FIG. 10B shows the device 10c after the component has been heat formed (e.g., around a spherical mandrel with recessed grooves) and with the markers 24, 26, 28 added. The forming mandrel not only creates a spherical shape of the final configuration but the recessed grooves in the mandrel also help space apart the filaments to create a relatively even spacing of the bioabsorbable filament (and thus equal spacing of gaps or openings to allow tissue infiltration) along and throughout the spherical surface of the device. FIG. 10C and FIG. 10) show top and side views, respectively of the device 10c embodiment shown in FIG. 10B.

Figure 11:
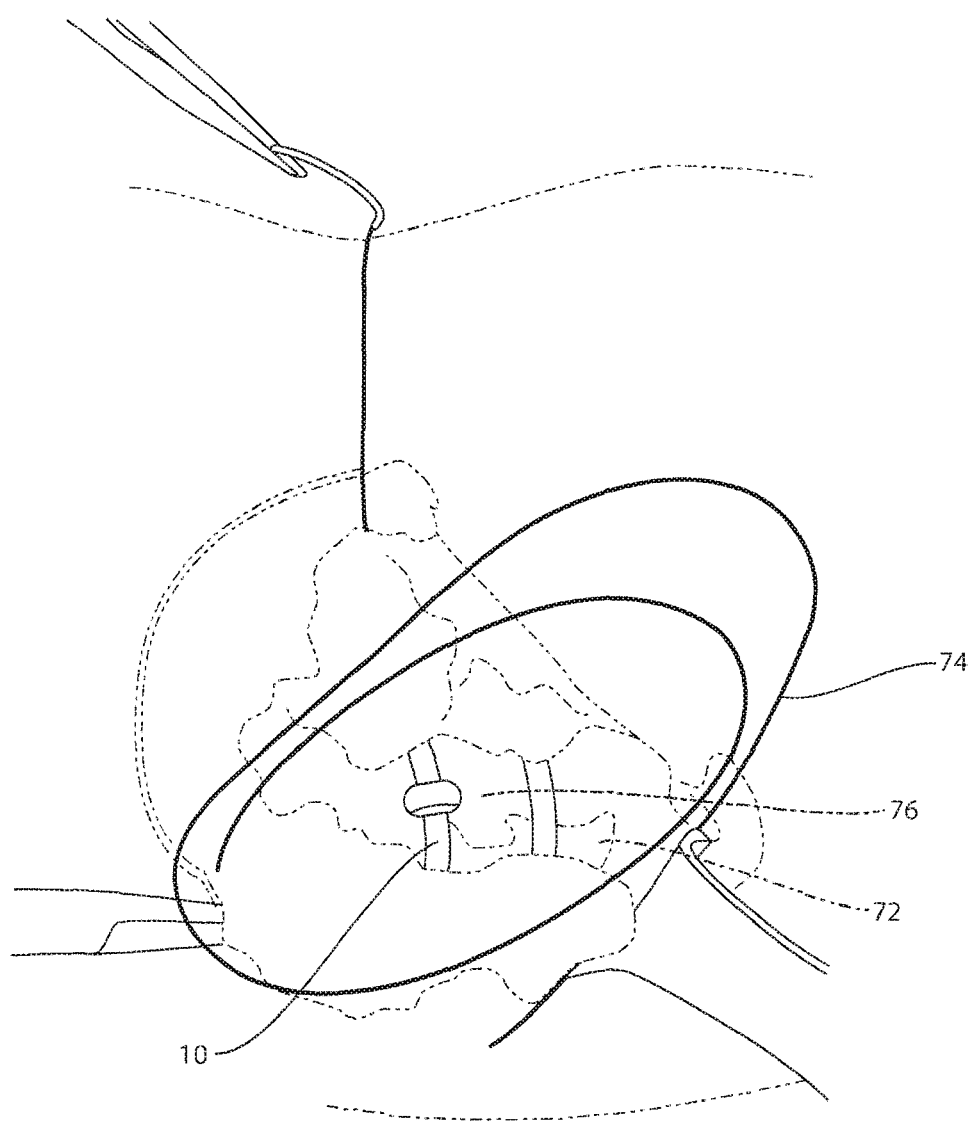
FIG. 11 illustrates an embodiment of an implant device that has been placed in a surgical resection cavity.

These types of devices can typically be used by surgeons who do not actively reapproximate the tissue (e.g. lumpectomy) cavity that they have created, as has been previously described herein. In addition, this device can also be used by surgeons who choose to surgically reapproximate at least a portion of the breast tissue surrounding the lumpectomy cavity. This reapproximation, sometimes called cavity closure, is typically accomplished (e.g. in the growing field of oncoplastic surgery) by suturing the breast tissue on either side of the lumpectomy cavity and drawing the tissue together (See FIG. 11) prior to skin closure. FIG. 11 shows a spiral marker 10 as described in FIG. 1 that has been placed in a lumpectomy cavity 72 of a patient's breast. As can be seen in the figure, the cavity is in the process of being closed with suture 74 and one can appreciate the tissue infiltrating 76 into the interstices of the spiral device 10. The open architecture of the device allows the tissue to flow or otherwise move within the peripheral boundary of the device as the tissue is pulled together and secured by suture. This device thus allows the surgical cavity site (and its margins) to be marked in a 3 dimensional fashion for subsequent imaging even though the lumpectomy cavity itself may be surgically altered or naturally altered in original size and/or shape. The lumpectomy cavity may be naturally (i.e. passively) altered in size or shape by partially or totally collapsing on itself or some cases by expanding due to seroma buildup within the lumpectomy cavity in the post-surgical period.

Figure 12:
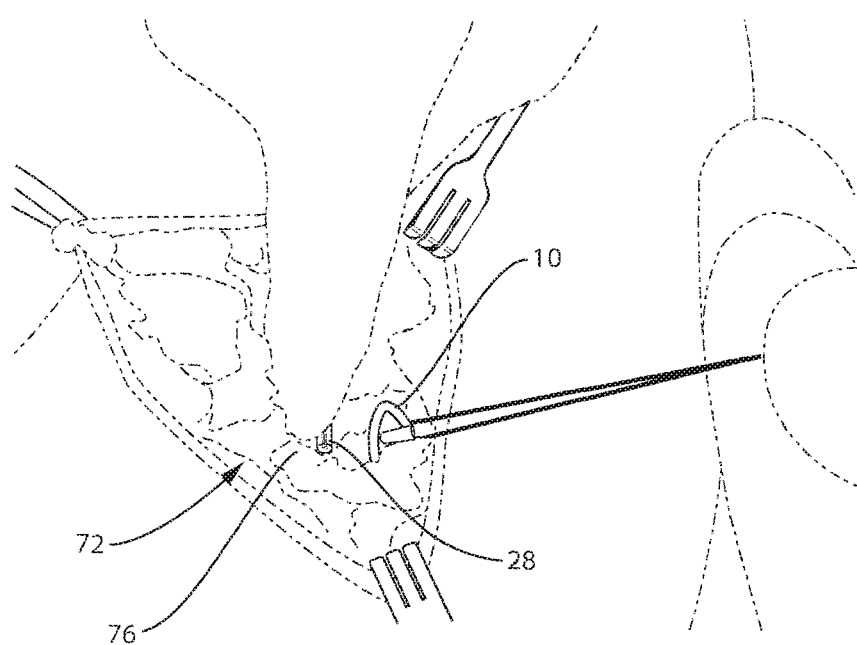
FIG. 12 illustrates another embodiment of an implant device that has been placed in a surgical resection cavity.

FIG. 12 shows a similar device 10 in another lumpectomy cavity 72 and one can appreciate the degree to which the surrounding tissue has infiltrated 76 within and flowed around the marker 28. Thus, these open architecture 3-dimensional tissue markers as described herein, allow the clinician to demarcate the closed and/or collapsed cavity with a level of 3-dimensional accuracy that has not previously been possible.

Figure 13:
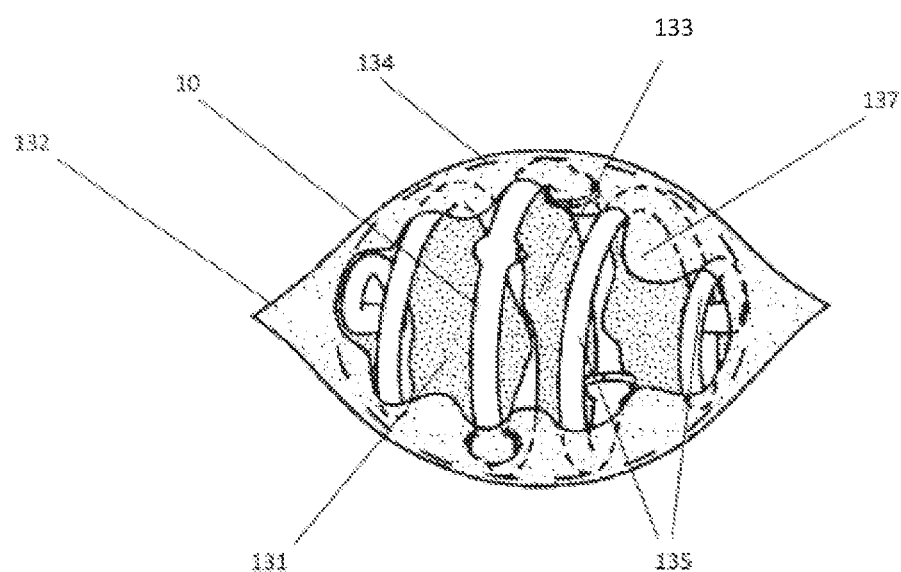
FIG. 13 illustrates another embodiment of an implant device that has been placed in a surgically created breast lumpectomy cavity.

FIG. 13 shows device 10 after placement in a lumpectomy cavity 131 at the time of surgery via a standard surgical incision 132. Because of the open architecture of the device 10, the breast and fatty tissues 133 at the margin of the lumpectomy cavity are able to naturally infiltrate across the peripheral boundary (dotted line 134) of the tissue marker device. The peripheral boundary 134 of the device is defined as the continuous overall surface shape that is defined by the outer regions or peripheral surface elements (for example 135) of the device. For the device 10 shown in FIG. 13, the peripheral boundary is an ovoid surface, a view of which is shown in this figure as an oval dotted line 134. Cavity boundary tissue can be seen to insinuate, penetrate, and/or flow between and around the elements of the device, thereby crossing the peripheral boundary of the device at for example, tissue locations 136 and 137.

The method of use for example, in a breast lumpectomy procedure is as follows: a lumpectomy cavity is created by surgically removing breast tissue via a skin incision (which may be minimally invasive, e.g. via tunneling from the areola), the cavity is sized using a sizer or other sizing method (e.g. direct examination of the lumpectomy specimen or cavity), the appropriately sized 3 dimensional open architecture bioabsorbable tissue marker is placed directly into the lumpectomy cavity via the surgical incision causing the breast tissue at the margin of the cavity to actively (e.g. via suture closure) or passively insinuate or otherwise move across the peripheral boundary of the tissue marker device, and then the wound or skin is closed in standard surgical fashion.

In yet another alternative method of use, the device is used as above but with the added step of passing some suture around one or more portions of the device and then passing the suture through adjacent tissue to tether or otherwise further secure the device to the adjacent tissue.

Figure 14:
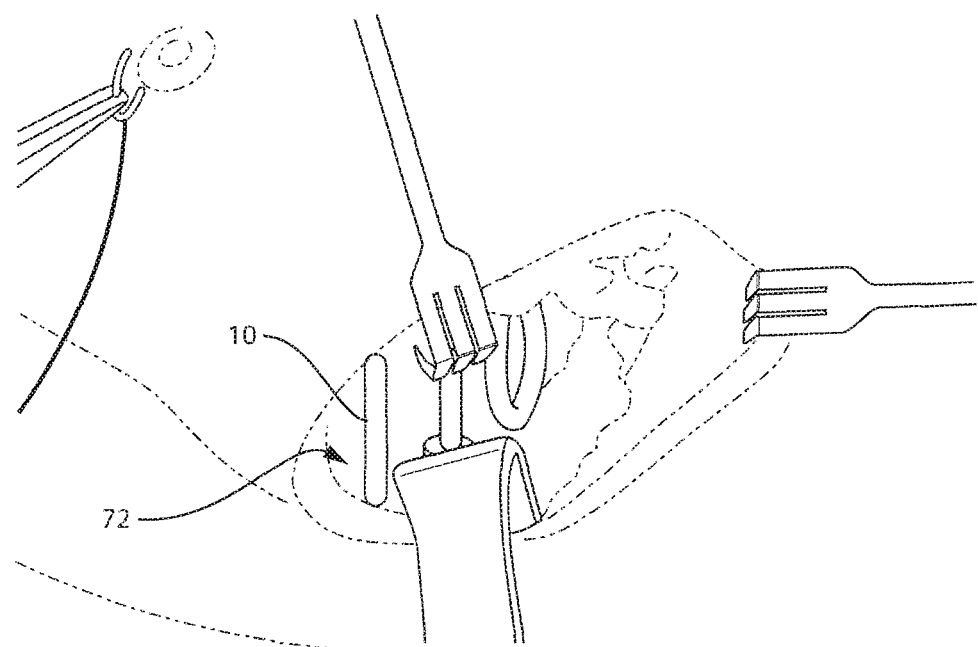
FIG. 14 illustrates another embodiment of an implant device that has been placed in a surgical resection cavity.

In some instances, the degree of tissue insinuation within the boundaries of the marker device (and hence the cavity) can be fairly limited. This instance can be appreciated in FIG. 14, where a marker device 10 of the type described in FIG. 1 has been placed in a lumpectomy cavity 72 of a patient's breast. One can see that in this approach, only a modest amount of tissue has infiltrated between the spiral elements and a significant portion of the original cavity remains free of tissue, with the marker device (including the marker clips) delineating the margins of the lumpectomy cavity.

Figure 15:
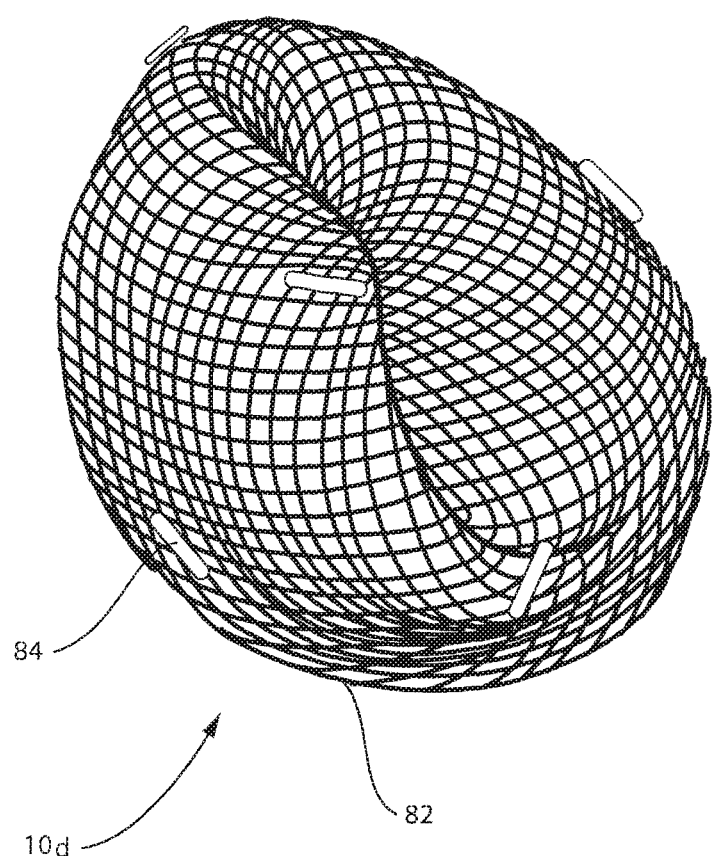
FIG. 15 illustrates an additional embodiment of an implant device of the invention.

FIG. 15 shows an alternate embodiment 10d where a mesh-like structure comprised of biodegradable filaments 82 is formed into a cavity-sized open-architecture shell-like structure with marker clips 84 secured at various peripheral locations of the structure. In one embodiment, the marker clips are still placed at the north and south poles and with four markers placed around the equator. This construction maximizes the overall diameter of the device while using a minimum mass of biodegradable material. The mesh-like structure (woven or braided filaments, or die-cut sheet) is also conformable yet still maintains a 3-dimensional volumetric characterization of the adjacent tissue as it resides within the cavity. The marker clips reside at the periphery of the device and hence optimizes visualization of the boundaries of the surgical cavity. The degree of tissue infiltration across the boundary of the device perimeter can be varied by the chosen gap size (e.g., from 1 mm to 10 mm). All versions within this gap size range are of an open-architecture design where fluids (e.g. blood, seroma, lymphatic fluid) can freely pass across the peripheral boundary of the device after implantation.

Figure 18:
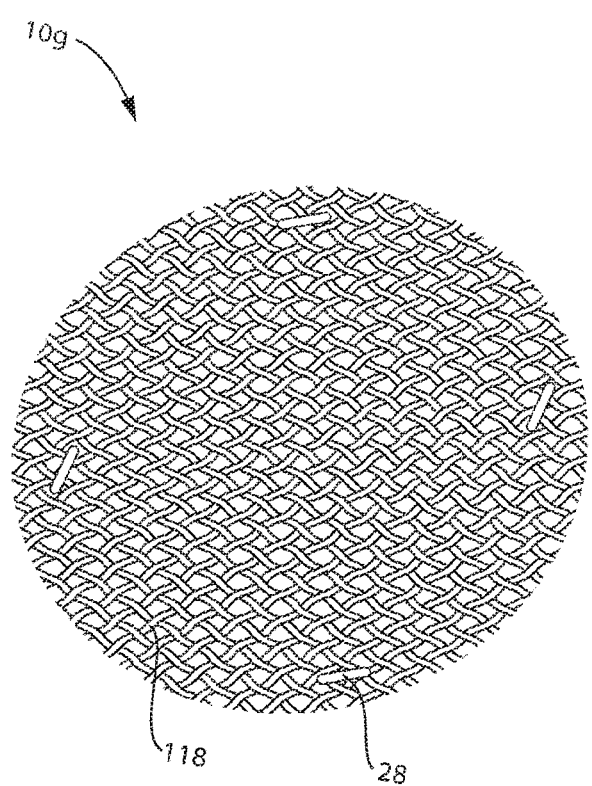
FIG. 18 illustrates an alternative 2-dimensional embodiment of an implant device of the invention.
Figure 19:
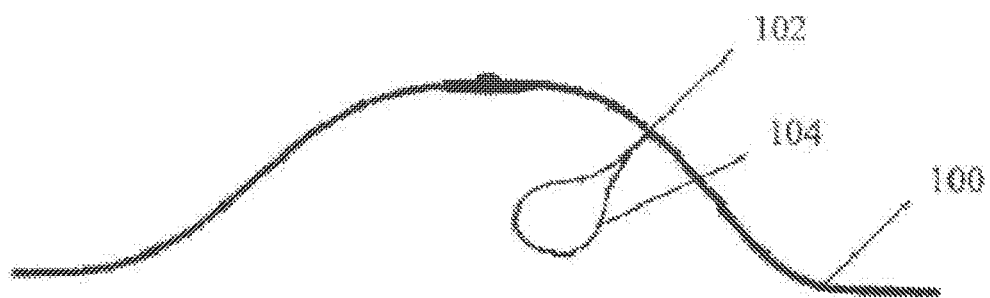
FIG. 19 illustrates an idealized tumor resection cavity in soft tissue as is known in the prior art.

A method according to the invention for treating these and other malignancies begins by surgical resection of a tumor site to remove at least a portion of the cancerous tumor and create a resection cavity as illustrated in FIG. 18. As illustrated, an entry site or incision 102 is created in patient 10) in order to remove tissue and create a cavity 104. Although FIG. 7 visually represents the surgical resection cavity in concept, it is important to note that most cavities are not that simplistically configured in the 2-8 week postoperative period that they are most likely to be visualized in the clinical imaging environment. For example, Landis et al ("Variability among breast radiation oncologists in delineation of the postsurgical lumpectomy cavity," 67(5) Int J Radiat Oncol Biol Phys 1299-308 (2007)) have documented the difficulty in delineating the cavity boundaries to be targeted in the postoperative period. Landis et al also document the range of sizes and shapes and geometric uncertainties that can be typically seen in the clinical environment. Tissue margins can be difficult to delineate due to uncertainty about the extent and position of the excision cavity and its adjacent tissue. Therefore, a device of the present invention that is placed into the surgical cavity at the time of cavity resection will demarcate these tissue boundaries at the time the cavity is surgically created, so that postoperatively (e.g. during the imaging required for subsequent radiation therapy) the tissue boundaries are much easier to identify (or identified with higher confidence as to their configuration and specific location). In some clinical environments, only the marker clips of the device will be visible and in other cases, the bioabsorbable carrier material may also be visible in addition to the marker clips. In either case, a more accurate delineation of the tissue adjacent to the lumpectomy cavity can be documented than would be possible had the marker device of the present invention not been placed, or had individual discrete marking devices (e.g. clips) been placed into the cavity as an alternative.

Following tumor resection, an implant of the invention (using any of the embodiments described herein) is placed into the tumor resection cavity 104. Placement can occur prior to closing the surgical site 102 such that the surgeon intra-operatively places the device, or alternatively, a device can be inserted after the initial surgical resection (e.g., during a re-excision to remove more tissue due to positive or inadequate surgical margins). In some cases, a new incision for introduction of the device may be created. In either case, the device, whose peripheral surface is preferably sized and configured to reproducibly demarcate the tissue surrounding the resection cavity 104, is placed within the resected tissue cavity.

Figure 16A:
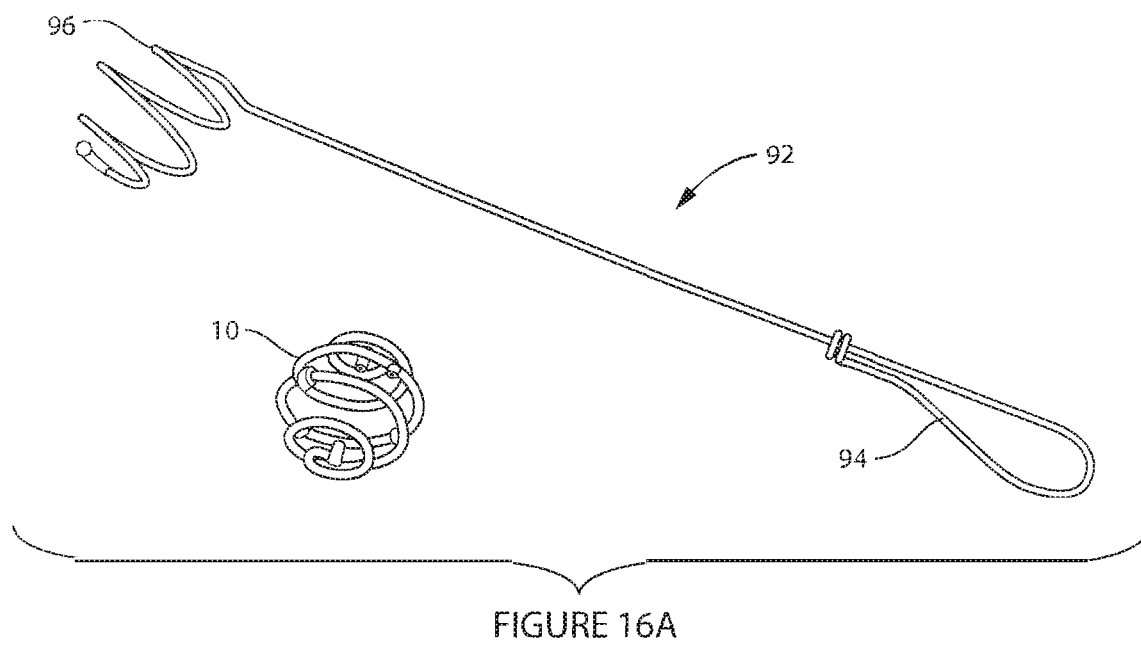
FIGS. 16A, B, and C illustrate sizing tools with corresponding spiral implant devices of the invention.
Figure 16B:
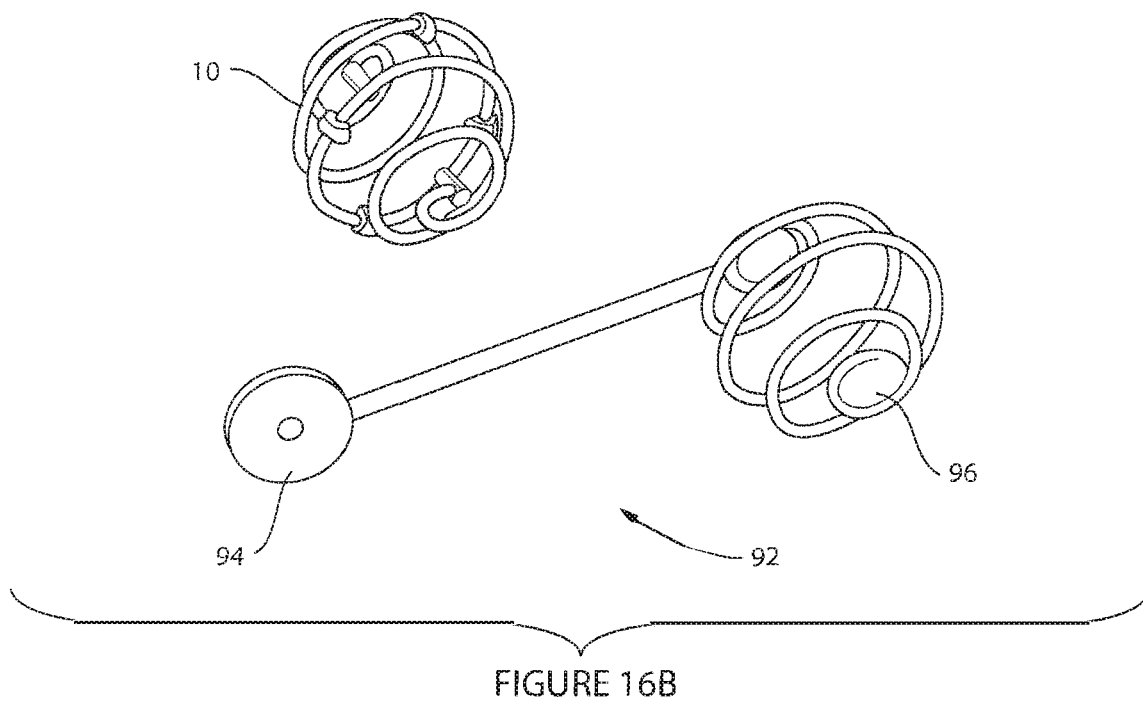
Figure 16C:
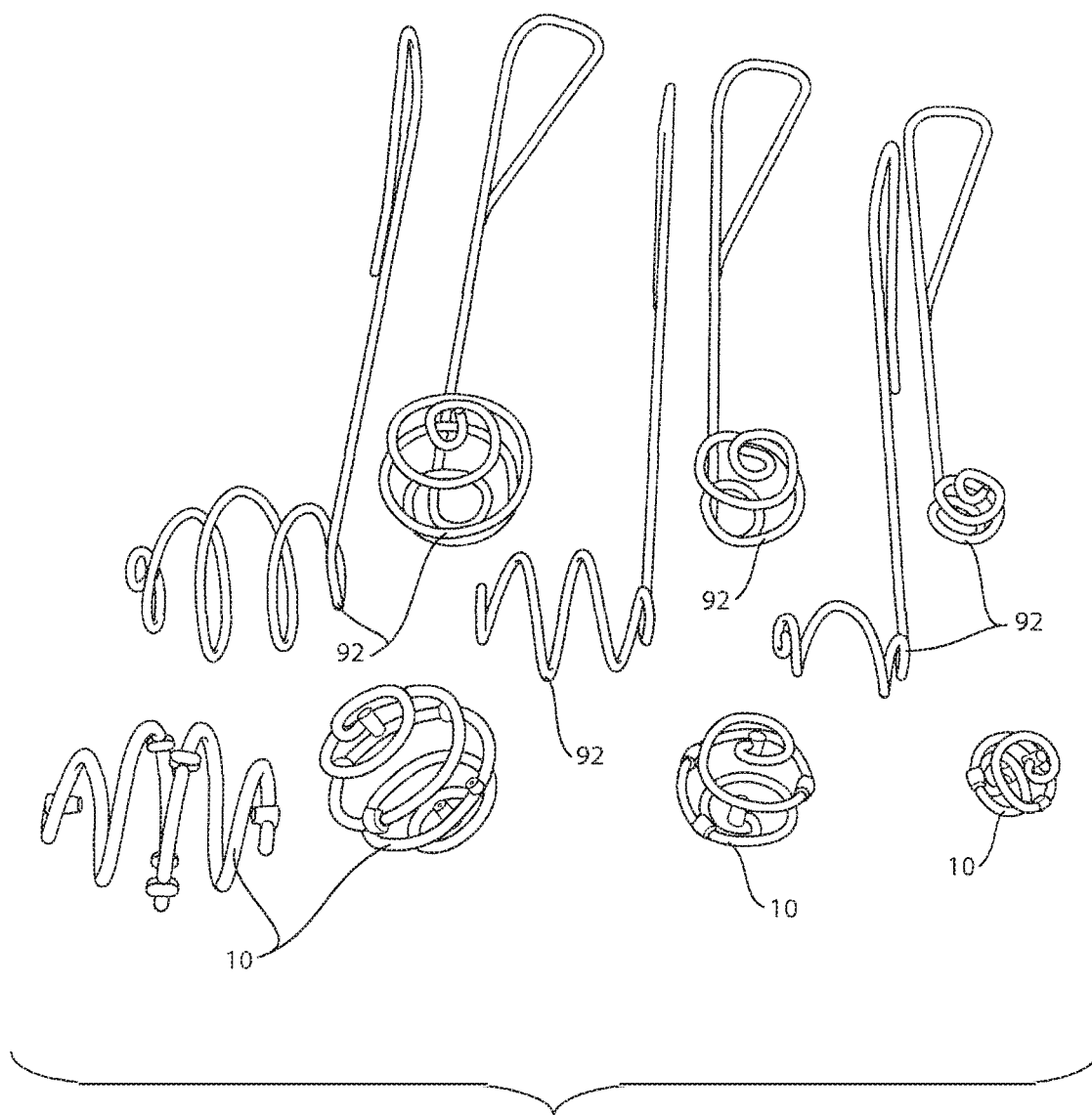

In some cases, it may be useful to employ a sizing tool in order to help the clinician choose the proper size and shape of device to be implanted for a given surgical cavity. It is particularly useful for the sizing tool to represent not only a similar general size (e.g. width and length) of the device to be implanted, but also to represent the general device configuration and/or device flexibility as well. With these attributes in mind, a sizing tool 92 is shown in FIGS. 16A and 16B. The exemplary sizing tool 92 includes a handle portion 94 and a sizing portion 96 that represents the size of a particular size of implantable device. Alongside the sizing tool 92 in the figure is an implantable device 10 that is represented by the sizing tool. FIG. 16C shows an array of such sizing tools 92 with their correspondingly sized and shaped implantable marker devices 10. In use, prior to selecting the specific size and shape of marker to implant, the clinician chooses a particular sizing tool from a set of reusable sterile sizing tools, such as that shown in FIG. 16C. While holding the handle of the sizing tool, the clinician places the spheroid end of the sizing tool into the surgical cavity. If desired, the tissue surrounding the tool may be surgically approximated by one or more temporary stitches or staples, to give the clinician a sense of how the tissue interacts with the sizing tool and hence how the tissue will interact around the implantable marker device. If the particular size or shape of the sizing tool is not optimal for the desired characteristics (e.g. wound tension, tissue cavity conformance), an alternately sized or shaped sizing tool may be used until the desired interaction with the surrounding tissue is achieved. Subsequently, the sizing tool is removed from the wound and the clinician selects the implant device that most closely matches the sizing tool configuration, and then places the implant device in the tissue cavity. Subsequently the breast tissue interacts with the implant in a fashion predicted by the sizer tool and the clinician closes the skin incision.

Following insertion of the implant device, such as by an open method or using a mini-open (e.g. tunneling) approach, the implant occupies (at least a portion of) the tissue cavity 104 and demarcates the surrounding target tissue until such time as the implant resorbs. When the implantable device is implanted in a resection cavity in soft tissue, a substantial portion of the device can conform to the walls of the resection cavity. "Substantial portion" is used herein in this context to mean greater than or equal to about 25% of the outward facing surface of the implant is in direct apposition to the surrounding tissue. Given the irregularities of many lumpectomy cavity shapes, not all of the surface of the implant may be in direct apposition to the surrounding tissue. Depending upon a variety of factors such as anatomy and surgical technique, there may often be voids filled by air or seroma. In some embodiments and clinical cases, the implant fully conforms to the surrounding tissue—where fully conforms means greater than or equal to about 95% of the implant's surface will be in direct apposition to surrounding tissue. Regardless of the percent of the device outer surface that comes in contact with the surrounding tissue, because of the open architecture of the device, there typically remains a portion of the resection cavity inner surface that does not come into contact with the implanted device. Otherwise the devices would not be of the open-architecture design, where there is free communication of fluids and tissue across the peripheral boundary of the device after implantation.

With the use of our invention, a defined tissue region is provided so that radiation can more accurately be delivered to the previously irregular or indeterminate tissue cavity walls. This defined surface can be delineated via a variety of imaging modalities such as ultrasound, MRI and CT or other x-ray by the bioabsorbable portion of the device or by the marker clips, or by both. In addition, the device may help reduce error in the treatment procedure introduced by tissue movement. The positioning and stabilization provided by the implant device may greatly improve the effectiveness of radiation therapy by facilitating radiation dosing and improving its accuracy. The result is a treatment method which concentrates radiation on target tissue and helps to minimize damage and preserve the surrounding healthy tissue. When the radiation dose is more precisely delivered, lower dose can be delivered to adjacent normal tissue, which improves the suitability for accelerated radiation treatment regimens (e.g., fewer dose fractions at a higher dose rate).

Prior to delivering radiation, but after placing the implant device, the device and the surrounding target tissue can preferably be visualized with an imaging device, including by way of non-limiting example, x-ray (kV or MV), conventional (2-D) mammography, 3-D mammography (including mammographic tomosynthesis, e.g., SELENIA Tomosynthesis by Hologic, Inc.), ultrasound, MRI, CT scan, PET, SPECT, and combinations thereof. These imaging devices provide a picture of the implant device and the surrounding target tissue to assist with the planning of external radiation therapy. Thus, the device can delineate the cavity boundaries so that a target volume may be derived. The device then provides a target for more accurate repositioning of the patient's targeted tissue immediately prior to each fraction of treatment. Finally, it can provide a means of real-time tracking the motion of the target volume so that the beams can either move with the target, can reshape dynamically to conform to a moving target or can be turned on and off as the target moves out of and back into the beams' path.

In the case of external beam radiation therapies such as three-dimensional conformal radiation therapy (3DCRT)

and IMRT, the imaging procedures provide a map of the residual tissue margin and assist with targeting tissue for radiation dosing. The radiation beams are then adapted for delivering a very precise radiation dose to the target tissue. Also, the improved targeting capability reduces the patient setup errors (target positioning relative to the treatment beam). Both factors improve target tissue conformality, reduce the radiation exposure to normal tissues surrounding the targeted volume of the body, and can allow for smaller target volumes than would otherwise be prescribed due to the decrease in uncertainty of the tissue margins of the cavity.

Some treatment regimens require repeated radiation dosing over a course of days or weeks, and the device can be used in those cases to repeatedly position the tissue surrounding the resected tumor cavity. These steps can be repeated as necessary over the course of a treatment regimen. Preferably, the implanted device remains in place without intervention, i.e., without removal or actions to change its configuration, throughout the course of treatment.

While the specific examples provided relate to treatment of cancer in the breast, the devices and procedures described herein may be used for other anatomic sites as well, (e.g. muscle for sarcoma, liver for liver tumors) including any regions where tissue is removed and the patient may require targeted radiation treatment at or near the site of tissue removal. The device may also be placed in the cavity created by the open surgical biopsy of high risk non-cancerous or ultimately benign breast lesions as well as other non-cancerous tissue sites. Doing so identifies the cavity for future breast imaging studies, which can be useful for long-term patient monitoring.

In addition to the 3-dimensional structures that have been described, there is also a clinical need to provide relatively 2-dimensional versions of the device as well. Whereas the 3-D devices demarcate the boundaries of more 3 dimensional structure (e.g., lumpectomy cavity) these 2-1) devices may be more useful to demarcate the more planar or curvilinear boundaries of tissue that may arise from surgical excision (e.g., during breast reduction).

Such planar yet compliant and conformable versions are shown in FIGS. 4, 5, and 17. These designs are useful for identifying the tissue boundaries that ultimately are re-approximated, actively or passively, during various surgical procedures. The surgical procedures that may benefit from these 2-dimensional designs are procedures that require excision of soft tissue followed by reapproximation of the resection boundaries (e.g., as in breast reduction or lung-wedge resections).

FIGS. 4 and 5 illustrate a spiral planar form of a 2-D style marker that can be placed surgically into a region of tissue that can be surgically approximated. The spiral elements are free to flex to conform to the tissue planes as the tissue is surgically approximated.

Figure 17A:
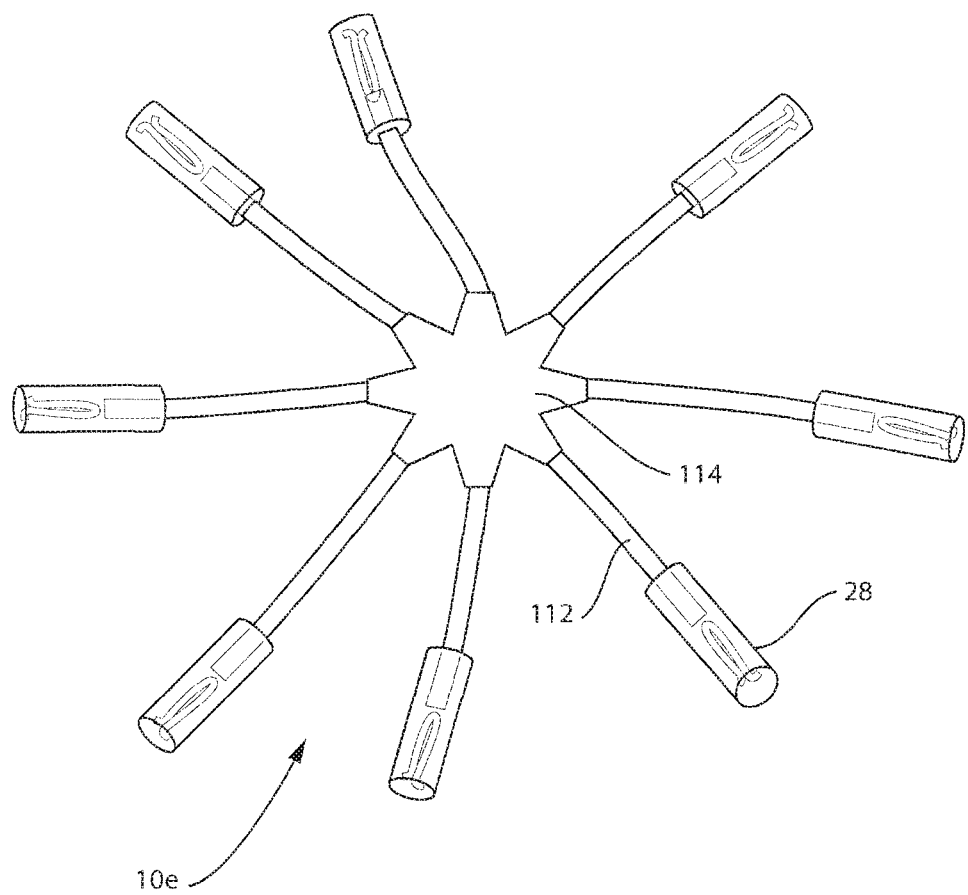
FIGS. 17A and B illustrate additional 2-dimensional embodiments of an implant device of the invention.

FIG. 17A illustrates another embodiment 10e comprising an array of flexible spines 112 made of a bioabsorbable polymer emanating from a central region 114. A radiopaque marker 28 of the type described previously resides at the extremity of each of the spines. A marker clip may reside at the central region as well (not shown). In use, the device is placed at the time of surgery along the surface of the region of tissue to be approximated. In many cases the tissue surfaces can be irregular in surface shape (e.g., non-planar) and so as the tissue surfaces may be approximated (e.g., by surgical suturing) yet the device is still able to flex and conform to the irregular surface shapes of the tissue surfaces. Again the open architecture of this structure allows for unencumbered fluid passage and tissue mobility while still demarcating the excised issue boundaries.

Figure 17B:
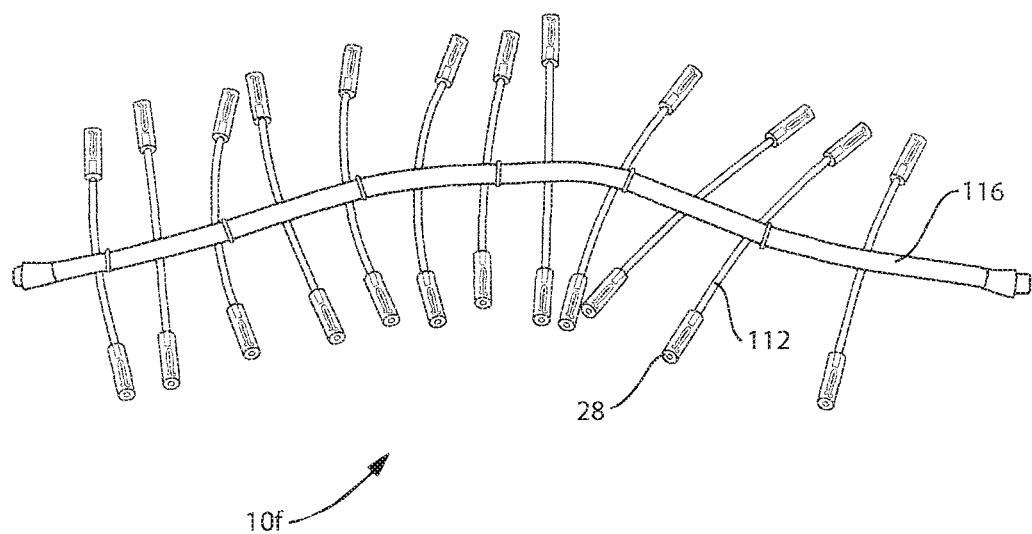

FIG. 17B illustrates yet another embodiment 10f similar to the device described with respect to FIG. 17A except that the central region 116 is a linear spine like element, which is also made of bioabsorbable material. Marker elements reside not only on the peripheral spines but also at periodic intervals along the central spine of the device. In use the device may be cut at various locations along the spine to best fit the anatomical site it is to be placed, prior to placement at the tissue site.

FIG. 18 illustrates yet another embodiment 10g where the device is comprised of a flexible bioabsorbable mesh or screen 118 that contain marker 28 elements that reside fixedly to the periphery or other locations along the flexible plane. In this embodiment radiopaque markers are comprised of Titanium wire elements that envelop the filaments of the mesh or screen material. In other embodiments (not shown), the wire elements may be enveloped within the bioabsorbable material and oriented either parallel or perpendicular to the generally planar flexible surface of the embodiment (as shown in FIG. 4B). One advantage of the perpendicular marker elements is that the marker elements may partially embed (like cleats of a shoe sole) into the adjacent tissue to secure the position of the device along the surface of the tissue to be approximated.

A person of ordinary skill in the art will appreciate further features and advantages of the invention based on the above-described embodiments. Accordingly, the invention is not to be limited by what has been particularly shown and described, except as indicated by the appended claims or those ultimately provided. All publications and references cited herein are expressly incorporated herein by reference in their entirety, and the invention expressly includes all combinations and sub-combinations of features included above and in the incorporated references.

The invention claimed is:

1. A method of fabricating a surgical implant, the method comprising:
   forming a two-dimensional planar structure from a bioabsorbable polymer; and
   shaping the two-dimensional planar structure into a three-dimensional, hollow spheroid support structure, the three-dimensional, hollow spheroid support structure having an open architecture and being sized and shaped to fill a surgically created cavity.

2. The method of claim 1, wherein forming the two-dimensional planar structure comprises injection molding the two-dimensional planar structure.

3. The method of claim 1, wherein forming the two-dimensional planar structure comprises extruding the two-dimensional planar structure.

4. The method of claim 1, wherein forming the two-dimensional planar structure comprises forming first and second planar spirals, the first planar spiral being opposite to the second planar spiral and connected to the second planar spiral via a connecting segment.

5. The method of claim 4, wherein forming the first planar spiral comprises forming a first polar region having a first extension and forming the second planar spiral comprises forming a second polar region having a second extension.

6. The method of claim 5, wherein the first extension and the second extension each include a pocket or an opening, and further including disposing respective first and second radio-opaque markers in each pocket or opening.

7. The method of claim 5, wherein shaping the two-dimensional planar structure into the three-dimensional, hollow spheroid support structure comprises forming a three-dimensional spiral having an equatorial region extending between the first polar region and the second polar region, wherein the first extension and the second extension each extend into and terminate within an open center of the three-dimensional spiral.

8. The method of claim 7, wherein the first extension and the second extension are coaxial with a longitudinal axis of the three-dimensional spiral, and wherein the first extension extends orthogonally from the first polar region at a first end portion of the three-dimensional spiral and the second extension extends orthogonally from the second polar region at a second end portion of the three-dimensional spiral.

9. The method of claim 8, further comprising connecting a strut between the first extension and the second extension.

10. The method of claim 1, further comprising, after forming the two-dimensional planar structure, securing a plurality of visualization markers to the two-dimensional planar structure.

11. The method of claim 10, wherein forming the two-dimensional planar structure includes forming a plurality of pockets in the two-dimensional planar structure, and wherein securing the plurality of visualization markers comprises inserting a respective visualization marker into each of the plurality of pockets.

12. The method of claim 10, wherein shaping the two-dimensional planar structure into the three-dimensional, hollow spheroid support structure comprises forming the three-dimensional, hollow spheroid support structure, with the plurality of visualization markers secured at various locations along a peripheral surface of the three-dimensional, hollow spheroid support structure.

13. The method of claim 1, wherein shaping the two-dimensional planar structure into the three-dimensional, hollow spheroid support structure comprises heat molding the two-dimensional planar structure.

14. The method of claim 13, wherein heat molding the two-dimensional planar structure comprises heat molding the two-dimensional planar structure around a spheroid forming mandrel.

15. The method of claim 1, wherein forming the two-dimensional planar structure comprises forming the two-dimensional planar structure in a two-part mold.

16. A method of fabricating a surgical implant, the method comprising:
    injection molding a two-dimensional body from a bioabsorbable polymer, the two-dimensional body comprising a first planar spiral terminating in a first end portion and a second planar spiral terminating in a second end portion, the first planar spiral being opposite to the second planar spiral and connected to the second planar spiral via a connecting segment; and
    heat molding the two-dimensional body into a three-dimensional spiral having an equatorial region extending between the first end portion and the second end portion.

17. The method of claim 16, wherein forming the first planar spiral comprises forming a first polar region having a first extension at the first end portion and forming the second planar spiral comprises forming a second polar region having a second extension at the second end portion.

18. The method of claim 17, wherein heat molding the two-dimensional body into the three-dimensional spiral comprises molding the first extension and the second extension to be coaxial with a longitudinal axis of the three-dimensional spiral, such that the first extension extends orthogonally from the first polar region into an open center of the three-dimensional spiral and the second extension extends orthogonally from the second polar region into the open center of the three-dimensional spiral.

19. The method of claim 18, further comprising connecting a strut between the first extension and the second extension.

20. The method of claim 16, wherein the first end portion and the second end portion each include a pocket or an opening, and further including disposing respective first and second radio-opaque markers in each pocket or opening.

21. A method of fabricating a surgical implant, the method comprising:
    forming a two-dimensional planar structure from a bioabsorbable polymer, the two-dimensional planar structure comprising a first polar region having a first extension and a second polar region having a second extension; and
    shaping the two-dimensional planar structure into a three-dimensional support structure having an equatorial region extending between the first polar region and the second polar region, wherein the first extension and the second extension each extend into and terminate within an open center of the three-dimensional support structure, and wherein the three-dimensional support structure has an open architecture and is sized and shaped to fill a surgically created cavity.

* * * * *